US008424388B2

(12) United States Patent
Mattes et al.

(10) Patent No.: US 8,424,388 B2
(45) Date of Patent: Apr. 23, 2013

(54) IMPLANTABLE CAPACITIVE PRESSURE SENSOR APPARATUS AND METHODS REGARDING SAME

(75) Inventors: Michael F. Mattes, Chandler, AZ (US); David A. Ruben, Mesa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 314 days.

(21) Appl. No.: 13/016,363

(22) Filed: Jan. 28, 2011

(65) Prior Publication Data

US 2012/0197155 A1 Aug. 2, 2012

(51) Int. Cl.
*G01L 7/00* (2006.01)

(52) U.S. Cl.
USPC ............ 73/700; 73/715; 73/718; 73/724; 600/485

(58) Field of Classification Search ............... None
See application file for complete search history.

(56) References Cited

U.S. PATENT DOCUMENTS

| | | | |
|---|---|---|---|
| 3,388,301 A | 6/1968 | James | |
| 3,943,557 A | 3/1976 | Frazee et al. | |
| 4,224,565 A | 9/1980 | Sosniak et al. | |
| 4,285,002 A | 8/1981 | Campbell | |
| 4,530,029 A | 7/1985 | Beristain | |
| 4,684,884 A | 8/1987 | Soderlund | |
| 4,701,826 A | 10/1987 | Mikkor | |
| 4,773,972 A | 9/1988 | Mikkor | |
| 4,775,831 A | 10/1988 | Annamalai | |
| 4,868,712 A | 9/1989 | Woodman | |
| 4,870,224 A | 9/1989 | Smith et al. | |
| 5,059,899 A | 10/1991 | Farnworth et al. | |
| 5,315,486 A | 5/1994 | Fillion et al. | |
| 5,381,039 A | 1/1995 | Morrison | |
| 5,381,804 A | 1/1995 | Shambroom | |
| 5,572,065 A | 11/1996 | Burns | |
| 5,592,391 A | 1/1997 | Muyshondt et al. | |
| 5,606,264 A | 2/1997 | Licari et al. | |
| 5,682,065 A | 10/1997 | Farnworth et al. | |

(Continued)

FOREIGN PATENT DOCUMENTS

| | | |
|---|---|---|
| EP | 0232935 | 8/1987 |
| EP | 1 128 174 A2 | 8/2001 |
| EP | 1864784 | 12/2007 |
| WO | 2008/044349 | 4/2008 |

OTHER PUBLICATIONS

U.S. Appl. No. 13/302,725, Nov. 22, 2011, Mueller et al.
U.S. Appl. No. 61/185,881, Jun. 10, 2001, Mueller et al.

(Continued)

*Primary Examiner* — Lisa Caputo
*Assistant Examiner* — Jermaine Jenkins
(74) *Attorney, Agent, or Firm* — Michael C. Soldner

(57) ABSTRACT

An implantable capacitive pressure sensor apparatus and method for making such an apparatus includes a first pressure sensor portion and a second pressure sensor portion. The first pressure sensor portion includes a diaphragm electrode connectable to ground (e.g., the diaphragm electrode being positioned in close proximity to the body when implanted therein such that the diaphragm electrode is deformable in response to pressure applied thereto by the body). The second pressure sensor portion includes a signal electrode (e.g., wherein the first pressure sensor portion and the second pressure sensor portion are coupled such that a gap is provided between the diaphragm electrode and the signal electrode) and an insulator material. The signal electrode is provided on and in direct contact with the insulator material to electrically isolate the signal electrode such that parasitic capacitance effects on the signal electrode are reduced.

39 Claims, 11 Drawing Sheets

U.S. PATENT DOCUMENTS

| | | |
|---|---|---|
| 5,837,562 A | 11/1998 | Cho |
| 5,938,956 A | 8/1999 | Hembree et al. |
| 5,955,789 A | 9/1999 | Vendramin |
| 6,022,787 A | 2/2000 | Ma |
| 6,032,064 A | 2/2000 | Devlin et al. |
| 6,074,891 A | 6/2000 | Staller |
| 6,144,866 A | 11/2000 | Miesel et al. |
| 6,145,384 A | 11/2000 | Ikeda et al. |
| 6,171,252 B1 | 1/2001 | Roberts |
| 6,221,024 B1 | 4/2001 | Miesel |
| 6,278,379 B1 | 8/2001 | Allen et al. |
| 6,287,256 B1 | 9/2001 | Park et al. |
| 6,297,072 B1 | 10/2001 | Tilmans et al. |
| 6,297,551 B1 | 10/2001 | Dudderar et al. |
| 6,298,255 B1 | 10/2001 | Cordero et al. |
| 6,303,977 B1 | 10/2001 | Schroen et al. |
| 6,323,550 B1 | 11/2001 | Martin et al. |
| 6,335,669 B1 | 1/2002 | Miyazaki et al. |
| 6,343,019 B1 | 1/2002 | Jiang et al. |
| 6,394,953 B1 | 5/2002 | Devlin et al. |
| 6,477,901 B1 | 11/2002 | Tadigadapa |
| 6,486,534 B1 | 11/2002 | Sridharan et al. |
| 6,500,694 B1 | 12/2002 | Enquist |
| 6,514,798 B2 | 2/2003 | Farnworth |
| 6,515,870 B1 | 2/2003 | Skinner et al. |
| 6,516,808 B2 | 2/2003 | Schulman |
| 6,539,253 B2 * | 3/2003 | Thompson et al. ............. 607/2 |
| 6,555,025 B1 | 4/2003 | Krupetsky |
| 6,555,856 B1 | 4/2003 | Staller |
| 6,563,133 B1 | 5/2003 | Tong |
| 6,566,596 B1 | 5/2003 | Askew |
| 6,566,736 B1 | 5/2003 | Ogawa et al. |
| 6,638,784 B2 | 10/2003 | Bartlett et al. |
| 6,696,369 B2 | 2/2004 | Fraser et al. |
| 6,718,206 B2 | 4/2004 | Casavant |
| 6,762,072 B2 | 7/2004 | Lutz |
| 6,774,327 B1 | 8/2004 | Wong |
| 6,821,342 B2 | 11/2004 | Mattes et al. |
| 6,822,326 B2 | 11/2004 | Enquist et al. |
| 6,855,115 B2 | 2/2005 | Fonseca et al. |
| 6,867,073 B1 | 3/2005 | Enquist |
| 6,874,367 B2 | 4/2005 | Jakobsen |
| 6,902,987 B1 | 6/2005 | Tong et al. |
| 6,903,918 B1 | 6/2005 | Brennan |
| 6,962,835 B2 | 11/2005 | Tong et al. |
| 6,968,743 B2 * | 11/2005 | Rich et al. ...................... 73/724 |
| 6,986,965 B2 | 1/2006 | Jenson |
| 7,041,178 B2 | 5/2006 | Tong et al. |
| 7,096,580 B2 | 8/2006 | Gonzalez et al. |
| 7,109,092 B2 | 9/2006 | Tong |
| 7,126,212 B2 | 10/2006 | Enquist et al. |
| 7,147,604 B1 | 12/2006 | Allen et al. |
| 7,150,195 B2 | 12/2006 | Jacobsen et al. |
| 7,162,926 B1 | 1/2007 | Guziak et al. |
| 7,205,181 B1 | 4/2007 | MacIntyre |
| 7,233,048 B2 | 6/2007 | Rybnicek |
| 7,238,999 B2 | 7/2007 | LaFond et al. |
| 7,247,517 B2 | 7/2007 | Rumer et al. |
| 7,305,889 B2 | 12/2007 | Fortin et al. |
| 7,318,264 B2 | 1/2008 | Schugt |
| 7,396,698 B2 | 7/2008 | Horning et al. |
| 7,403,818 B2 | 7/2008 | Kramer et al. |
| 7,462,552 B2 | 12/2008 | Tong et al. |
| 7,485,968 B2 | 2/2009 | Enquist et al. |
| 7,495,462 B2 | 2/2009 | Hua et al. |
| 7,540,188 B2 | 6/2009 | Wiese et al. |
| 7,553,582 B2 | 6/2009 | Bates |
| 7,563,692 B2 | 7/2009 | Fortin et al. |
| 7,599,737 B2 * | 10/2009 | Yomtov et al. .................... 607/3 |
| 7,622,324 B2 | 11/2009 | Enquist et al. |
| 7,647,836 B2 | 1/2010 | O'Brien et al. |
| 7,748,277 B2 | 7/2010 | O'Brien et al. |
| 7,759,774 B2 | 7/2010 | Fraser et al. |
| 7,778,679 B2 * | 8/2010 | Schulman et al. ............ 600/345 |
| 7,781,250 B2 | 8/2010 | Wang et al. |
| 7,829,363 B2 | 11/2010 | You |
| 7,886,608 B2 | 2/2011 | Mothilal et al. |
| 7,902,851 B2 | 3/2011 | Fenner et al. |
| 8,072,056 B2 | 12/2011 | Mueller et al. |
| 8,125,058 B2 * | 2/2012 | Mueller et al. ................ 257/659 |
| 8,145,324 B1 * | 3/2012 | Stevenson et al. ............ 607/122 |
| 8,172,760 B2 * | 5/2012 | Mattes et al. ................. 600/485 |
| 2001/0033024 A1 | 10/2001 | Fraser et al. |
| 2002/0115920 A1 | 8/2002 | Rich et al. |
| 2004/0012083 A1 | 1/2004 | Farrell |
| 2004/0079277 A1 | 4/2004 | Mattes et al. |
| 2004/0082145 A1 | 4/2004 | Reichenbach |
| 2004/0186396 A1 | 9/2004 | Roy et al. |
| 2004/0222478 A1 | 11/2004 | Zhang et al. |
| 2005/0009246 A1 | 1/2005 | Enquist et al. |
| 2005/0065565 A1 | 3/2005 | Kramer et al. |
| 2005/0151151 A1 | 7/2005 | Hawtof |
| 2005/0284815 A1 | 12/2005 | Sparks |
| 2006/0033204 A1 | 2/2006 | Fraser et al. |
| 2006/0110854 A1 | 5/2006 | Horning et al. |
| 2006/0264004 A1 | 11/2006 | Tong et al. |
| 2006/0267167 A1 | 11/2006 | McCain |
| 2006/0273430 A1 | 12/2006 | Hua et al. |
| 2007/0037379 A1 | 2/2007 | Enquist et al. |
| 2007/0107524 A1 | 5/2007 | O'Brien et al. |
| 2007/0158769 A1 | 7/2007 | You |
| 2007/0179545 A1 | 8/2007 | Warkentin et al. |
| 2007/0199385 A1 | 8/2007 | O'Brien et al. |
| 2007/0251338 A1 | 11/2007 | Wiese et al. |
| 2007/0261497 A1 | 11/2007 | O'Brien et al. |
| 2007/0269921 A1 | 11/2007 | You |
| 2008/0027332 A1 | 1/2008 | Bradley |
| 2008/0102096 A1 | 5/2008 | Molin |
| 2008/0312726 A1 | 12/2008 | Frank et al. |
| 2009/0057868 A1 | 3/2009 | Wang et al. |
| 2009/0270707 A1 | 10/2009 | Alfoqaha et al. |
| 2009/0308169 A1 | 12/2009 | Mothilal et al. |
| 2010/0262208 A1 | 10/2010 | Parker |
| 2010/0263794 A1 | 10/2010 | George |
| 2010/0304151 A1 | 12/2010 | Tuennermann |
| 2010/0314149 A1 | 12/2010 | Gerrish et al. |
| 2010/0314726 A1 | 12/2010 | Mueller et al. |
| 2010/0314733 A1 | 12/2010 | Mueller et al. |
| 2010/0315110 A1 | 12/2010 | Fenner et al. |
| 2010/0324614 A1 | 12/2010 | Mueller et al. |

OTHER PUBLICATIONS

U.S. Appl. No. 61/229,867, Jul. 30, 2009, Mueller et al.
U.S. Appl. No. 61/229,869, Jul. 30, 2009, Larson et al.
U.S. Appl. No. 61/235,745, Aug. 21, 2009, Gerrish et al.
Lea et al., "DRIE from MEMS to wafer-level packaging," *Solid State Technology*, Dec. 2007; 50(12), 8 pgs. Retrieved online on Oct. 11, 2010. Available online at <url:http://www.electroiq.com/ElectroIQ/en-us/index/display/Semiconductor_Article_Tools_Template.articles.solid-state-technology.volume-50.issue-12.features.mems.drie-from-mems-to-wafer-level-packaging.html>.
Pham et al., "High-aspect-ratio bulk micromachined vias contacts," ProcSAFE & Prorisc 2004, Veldhoven, NL, Nov. 25-26, 2004, pp. 742-746.
Potkay, "Long Term, Implantable Blood Pressure Monitoring Systems," *Biomed Microdevices*, 2008; 10:379-392. Published online Dec. 20, 2007.
U.S. Appl. No. 12/912,433, Oct. 26, 2010, Danzi.
U.S. Appl. No. 12/977,890, Dec. 23, 2010, Ruben.
EnerChip™, CBC012, Rechargeable Solid State Energy Storage: 12μAh, 3.8V, Cymbet Corporation, DS-72-02 Rev. A, 2009-2010 Cymbet™ Corporation (5 pp.).
Gillner et al., "Laser Bonding of Micro Optical Components," *Proceedings of SPIE*, vol. 4941, pp. 112-120, Oct. 30, 2003.
Park, "Characterization of Transmission Laser Bonding (TLB) Technique for Microsystem Packaging," Arizona State University, May 2006 (135 pgs.).
Sari et al., "Applications of Laser Transmission Processes for the Joining of Plastics, Silicon and Glass Micro Parts," *Microsyst Technol*. (2008) 14:1879-1886, published online Jul. 18, 2008.
Theppakuttai et al., "Localized Laser Transmission Bonding for Microsystem Fabrication and Packaging," *Journal of Manufacturing Processes*, vol. 6, No. 1, 2004 (8 pgs.).

Thinergy, The Leading Thin Power Solution, 2010 Infinite Power Solutions, Inc. (2 pp.) accesslined online Oct. 14, 2010 at http://www.infinitepowersolutions.com/product/thinergy.

Wiemer et al., "Developments Trends in the Field of Wafer Bonding Technologies," 214th ESC Meeting, Abstract #2229, Oct. 12-17, 2008, Honolulu, HI (1 pg.).

Wild et al., "Locally Selective Bonding of Silicon with Glass with Laser," *Sensors and Actuators A: Physical*, vol. 93, Issue 1, Aug. 25, 2001, p. 63-69.

Witte et al., "Laser Joining of Glass with Silicon," *Proceedings of SPIE*, vol. 4637, Jan. 21, 2002, pp. 487-495.

International Search Report and Written Opinion for PCT/US2011/034542; 11 pgs.

U.S. Appl. No. 61/406,961, Oct. 26, 2010, O'Brien.

Lau, "MEMS Structures for Stress Measurements for Thin Films Deposited Using CVD," Master of Science Thesis, Massachusetts Institute of Technology, Feb. 2001, 79 pgs.

Oberg et al., Machinery's Handbook, 25th edition, Industrial Press, New York, NY, 1996; title page, copyright page and p. 267. 2 pages total.

Osterberg et al., "M-Test: A Test Chip for MEMS Using Electrostatically Actuated Test Structures" *Journal of Microelectromechanical Systems*, Jun. 1997; 6(2): 107-118.

* cited by examiner

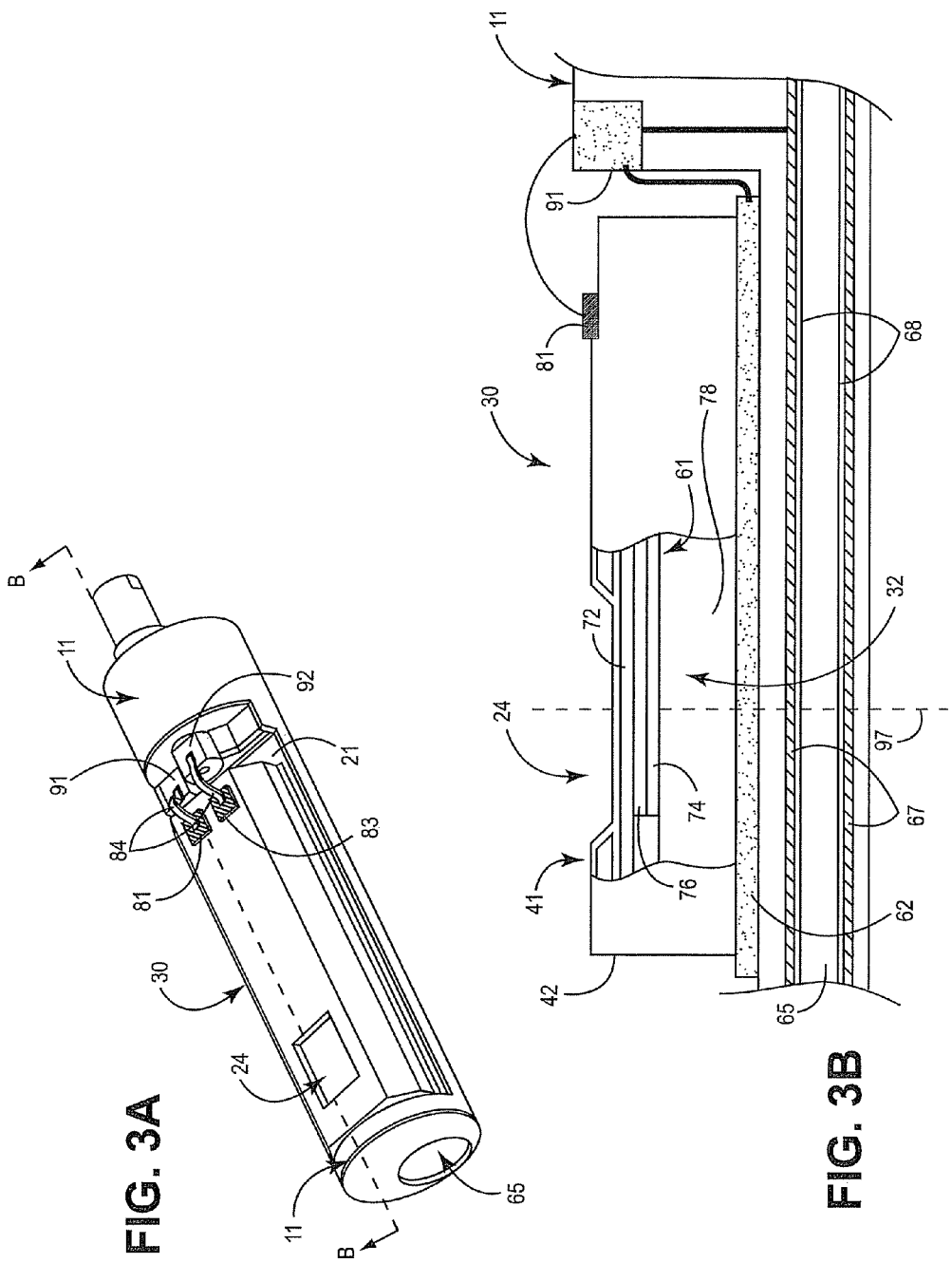

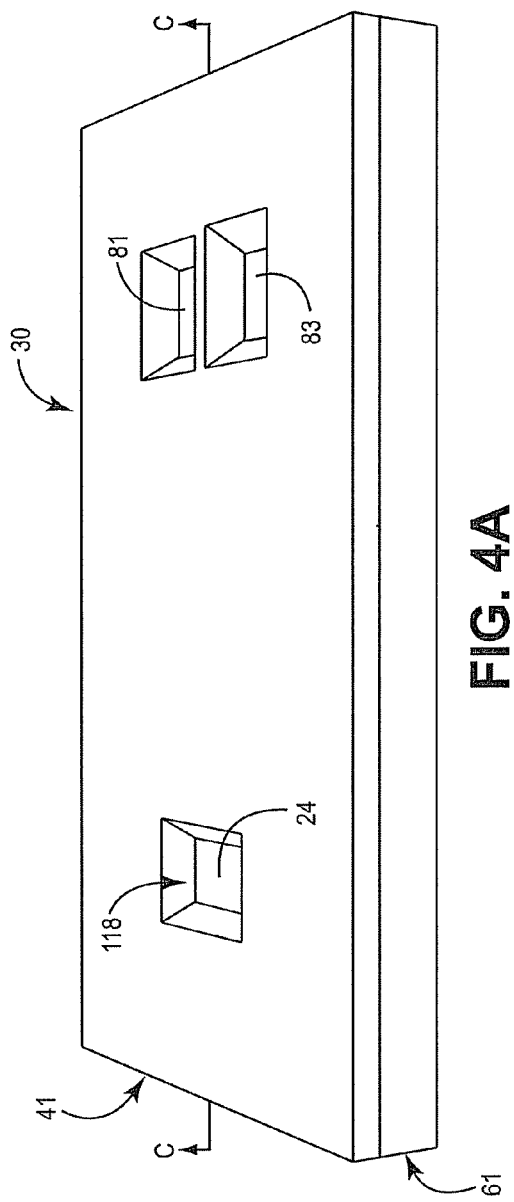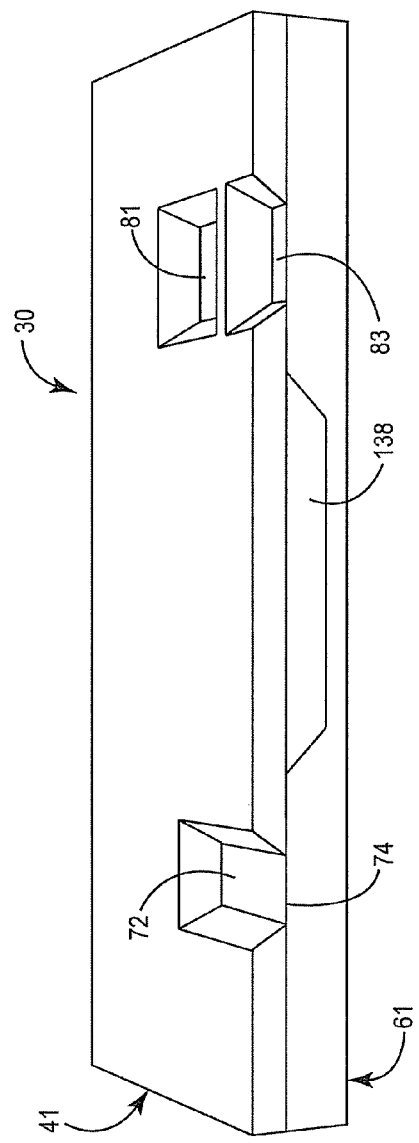
FIG. 4A
FIG. 4B

IMPLANTABLE CAPACITIVE PRESSURE SENSOR APPARATUS AND METHODS REGARDING SAME

BACKGROUND

The present disclosure relates to capacitive pressure sensors (e.g., in-vivo pressure sensors, such as implantable pressure sensors) and methods of providing such pressure sensors.

Implantable systems for cardiac rhythm management often employ medical electrical leads, which extend into the venous blood stream and couple a therapy delivery generator device to a surface of the heart. For example, a medical electrical lead may include one or more electrodes for stimulating the heart and/or for sensing electrical activity of the heart.

In addition to, or in lieu of electrodes, a medical electrical lead may include one more other types of sensors, for example, a pressure sensor. Many of such pressure sensors are micro-electromechanical system (MEMS) pressure transducers, such as piezo-resistive MEMS pressure sensors. Other MEMS pressure sensors may be MEMS capacitive pressure transducers. Such a pressure sensor may include a hermetically sealed capsule that contains a gap capacitor and an integrated circuit (IC) chip coupled thereto. The IC chip may be connected to external contacts, source and ground, and such contacts may be coupled to conductors extending within the lead body. Examples of one or more pressure sensors are described in United States Patent Application Publication No. 2007/0107524 entitled "Hermetic Chamber with Electrical Feedthroughs" published 17 May 2007; United States Patent Application Publication No. 2007/0199385 entitled "Capacitor Electrode Formed on Surface of Integrated Circuit Chip" published 30 Aug. 2007; and United States Patent Application Publication No. 2009/0308169 entitled "Pressure Sensor Configurations for Implantable Medical Electrical Leads" published 17 Dec. 2009; which are hereby incorporated by reference in their entirety.

Small capacitive pressure sensors may encounter parasitic capacitive problems, e.g., sensitivity of such pressure sensors drops drastically with the addition of parasitic capacitance. This is especially the case when the capacitive pressure sensor is in close contact with body tissues and fluids, such as an in-vivo device (e.g., an implantable capacitive pressure sensor).

SUMMARY

The disclosure herein relates generally to in-vivo capacitive pressure sensor apparatus and methods regarding such pressure sensor apparatus (e.g., methods for forming one or more portions of such capacitive pressure sensor apparatus) that reduce, for example, parasitic capacitance effects on the pressure sensor apparatus. For example, in one or more embodiments, to reduce parasitic capacitance effects, the diaphragm electrode of the capacitive pressure sensor apparatus may be put in contact with the in-vivo environment at ground potential while the signal electrode of the capacitive pressure sensor apparatus is isolated with an insulating material (e.g., glass or other biostable insulator).

For example, one exemplary pressure sensor apparatus (e.g., an implantable pressure sensor, a pressure sensor apparatus provided as part of a lead, or a pressure sensor apparatus provided as a wireless pressure sensor apparatus) may include a first pressure sensor portion and a second pressure sensor portion. The first pressure sensor portion may include a diaphragm electrode connectable to ground (e.g., the diaphragm electrode may be positioned in close proximity to the body when implanted therein such that the diaphragm electrode is deformable in response to pressure applied thereto by the body. The second pressure sensor portion may include a signal electrode (e.g., the first pressure sensor portion and the second pressure sensor portion provide a gap between the diaphragm electrode and the signal electrode) and an insulator material. The signal electrode is provided on and in direct contact with the insulator material to electrically isolate the signal electrode such that parasitic capacitance effects on the signal electrode caused by electrical activity in the body when the pressure sensor apparatus is implanted therein are reduced. Further, the diaphragm electrode is grounded when the implantable pressure sensor apparatus is implanted in the body to shield the signal electrode from electrical activity in the body.

Further, for example, one exemplary method of providing a pressure sensor apparatus may include providing a first pressure sensor portion that includes a diaphragm electrode connectable to ground (e.g., wherein the diaphragm electrode is positioned in close proximity to the body when implanted therein such that the diaphragm is deformable in response to pressure applied thereto by the body) and providing a second pressure sensor portion that includes a signal electrode relative to the first pressure sensor portion to provide a gap between the diaphragm electrode and the signal electrode. The second pressure sensor portion further includes an insulator material, wherein the signal electrode is provided on and in direct contact with the insulator material to electrically isolate the signal electrode such that parasitic capacitance effects on the signal electrode caused by electrical activity in the body when the pressure sensor apparatus is implanted therein are reduced. Further, the diaphragm electrode is grounded when the implantable pressure sensor apparatus is implanted in the body to shield the signal electrode from electrical activity in the body.

In one or more embodiments, the second pressure sensor portion may include a glass substrate material extending from a first side surface to a second side surface opposite the first side surface (e.g., wherein the signal electrode is provided on and in direct contact with the first side surface of the glass substrate material); or the second pressure sensor portion may include a substrate material having at least one trench formed through at least a portion thereof (or entirely) with the at least one trench filled with an insulator material (e.g., wherein the signal electrode is provided on and in direct contact with the insulator material, such as a glass material).

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

The following drawings are illustrative of particular embodiments of the present disclosure and therefore do not limit the scope of the invention. The drawings are not to scale (unless so stated) and are intended for use in conjunction with the explanations in the following detailed description. Embodiments of the present disclosure will hereinafter be described in conjunction with the appended drawings, wherein like numerals denote like elements.

FIG. 3A is a perspective view of one embodiment of a subassembly including a pressure sensor apparatus mounted on a platform portion of a lead body.

FIG. 3B is longitudinal view of a portion of the subassembly shown in FIG. 3A with a cut away portion showing a cross-section view thereof taken along line B-B of FIG. 3A.

FIG. 4A is a perspective view of one embodiment of a pressure sensor apparatus such as, for example, that shown generally in FIG. 2.

FIG. 4B is a cross-section perspective view of the pressure sensor apparatus shown in shown in FIG. 4A taken along line C-C thereof.

DETAILED DESCRIPTION OF EXEMPLARY EMBODIMENTS

Figure 1:
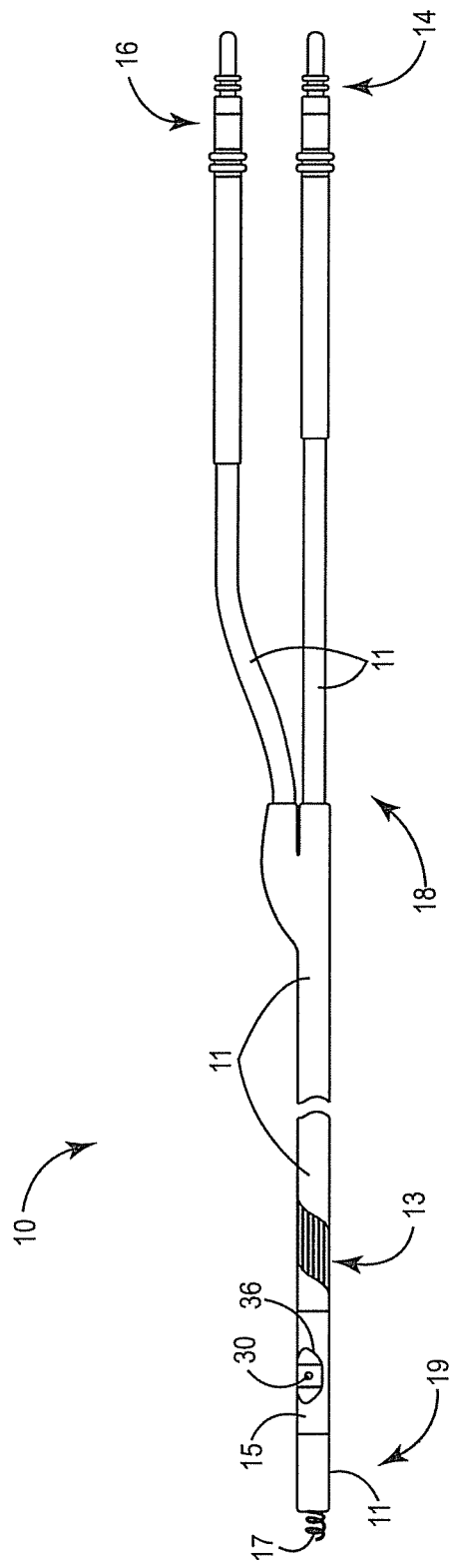
FIG. 1 is a plan view, with a cut-way portion, of one embodiment of a medical electrical lead.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Exemplary methods and apparatus shall be described with reference to FIGS. 1-7. It will be apparent to one skilled in the art that elements or processes from one embodiment may be used in combination with elements or processes of the other embodiments, and that the possible embodiments of such methods and apparatus using combinations of features set forth herein is not limited to the specific embodiments shown in the Figures and/or described herein. For example, techniques used for reducing parasitic capacitance effects for a pressure sensor apparatus used in a lead may also be used for a wireless pressure sensor apparatus. Still further, for example, techniques for isolating signal electrodes or grounding diaphragm electrodes described with respect to one embodiment may be applied to one or more other embodiments. Yet further, concepts for providing the gap of the capacitor described with respect to one embodiment may be applied to one or more other embodiments. Further, it will be recognized that the embodiments described herein may include many elements that are not necessarily shown to scale. Still further, it will be recognized that the processes and the size and shape of various elements herein may be modified but still fall within the scope of the present disclosure, although certain processes, one or more shapes and/or sizes, or types of elements, may be advantageous over others.

FIG. 1 is a plan view of an exemplary medical electrical lead 10 according to one embodiment. FIG. 1 illustrates lead 10 including an insulative lead body 11 which is terminated at a proximal end 18 with a pair of connectors 14, 16 and is terminated at a distal end 19 by a tip electrode 17. According to the illustrated embodiment, a pressure sensor apparatus 30 is mounted to lead body 11, and another electrode 15 extends about pressure sensor 30. Electrode 15 includes an aperture 36, for example, to expose a pressure sensitive diaphragm portion 24 of pressure sensor apparatus 30, which is seen in the exploded perspective view of FIG. 2.

Figure 2:
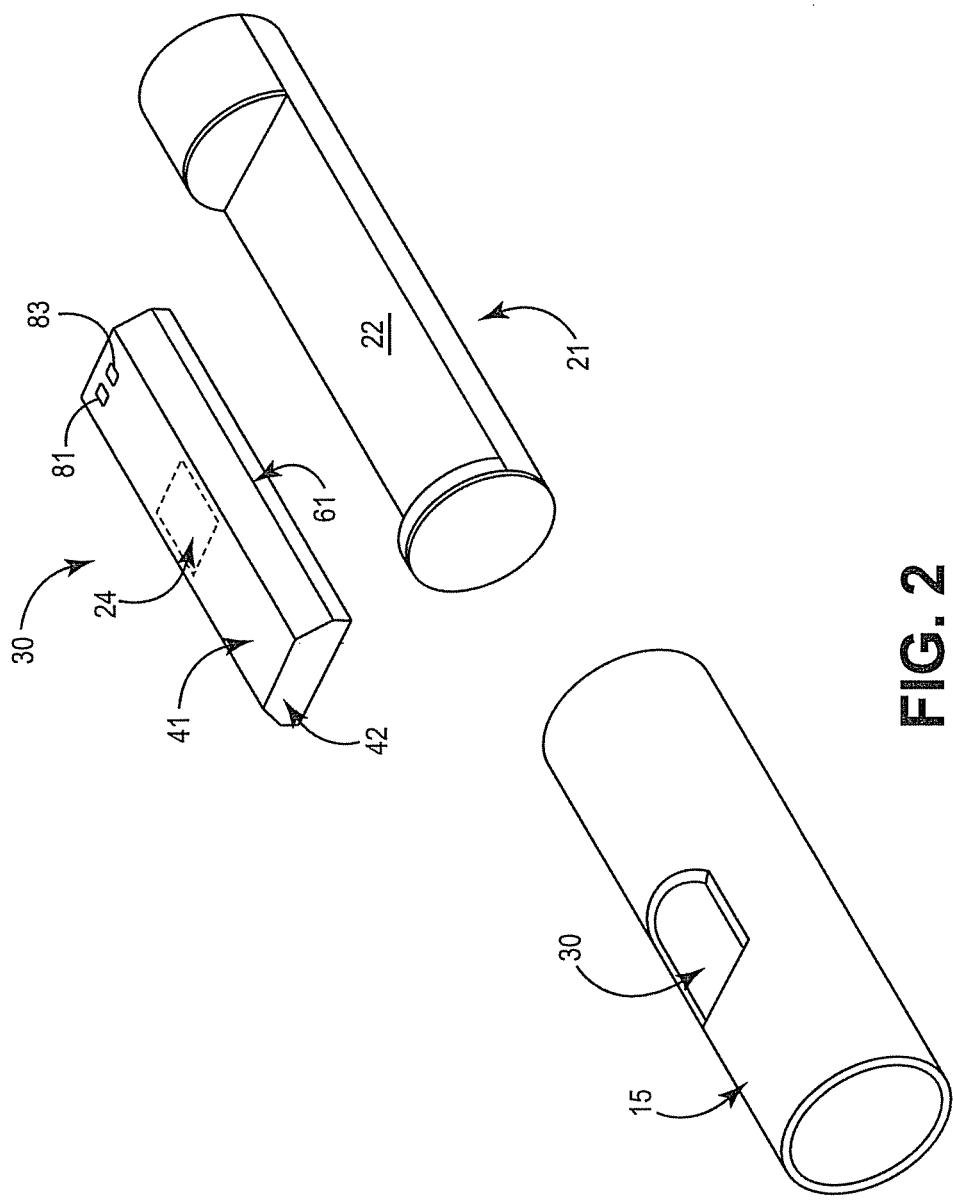
FIG. 2 is an exploded perspective view of a portion of the lead shown in FIG. 1 including a capacitive pressure sensor apparatus.

FIG. 2 illustrates an exemplary platform portion 21 of lead body 11 including a mounting surface 22 on which pressure sensor apparatus 30 is mounted, for example, being adhered thereto, via adhesive bonding. Platform portion 21 may be separately formed, for example, molded from a relatively rigid plastic, and adapted for integration into lead body 11. Although not shown in FIG. 2, platform portion 21 preferably includes conduits allowing for a plurality of conductors 13 to couple with pressure sensor apparatus 30 and electrodes 15, 17. Platform portion 21, pressure sensor apparatus 30 and electrode 15 may be integrated into lead body 11, for example, as described in commonly-assigned and co-pending U.S. Patent Application Publication No. 2009/0270707 A1, published 29 Oct. 2009 and entitled "Sensor Assemblies for Implantable Medical Electrical Leads," which is hereby incorporated by reference in its entirety.

Pressure sensor apparatus 30 is preferably constructed according to microelectromechanical systems (MEMS) fabrication methods and includes a capacitive pressure transducer including a gap capacitor contained within a package or housing having sidewalls 42, for example, formed of materials including, for example, a biocompatible ceramic, such as glass, fused silica, sapphire quartz or silicon. Package sidewalls 42 of the exemplary pressure sensor apparatus 30 are shown as being formed by a first pressure sensor portion 41, e.g., a lid portion, and a second pressure sensor portion 61, e.g., a base portion. For example, the first pressure sensor portion 41 includes pressure-sensitive diaphragm portion 24 (e.g., a diaphragm portion including a diaphragm electrode 72 as shown, for example, in FIG. 3B), and is coupled to base portion 61 which includes a signal electrode 74 separated from the diaphragm electrode 72 by a gap 76. For example, the first pressure sensor portion 41 may be coupled to the second pressure sensor portion 61 by a bonding process, such as a laser fusing process, to form the gap 76 (and, in one or more embodiments, one or more additional sealed cavities therebetween).

FIG. 3A is a perspective view of pressure sensor apparatus 30 mounted on platform portion 21 integrated with a lead body 11 (e.g., cradle for interfacing with the lead body) and electrically connected within the electrical lead 10 (e.g., a lead having a lead diameter of 10 fr or less). FIG. 3B is a longitudinal view with a cut-away portion showing a cross-section taken through line B-B of FIG. 3A. The cross-section portion of FIG. 3B illustrates a gap capacitor 32 which is contained by the package sidewalls 42, and which includes the diaphragm electrode 72 (e.g., a diaphragm electrode plate or other conductive structure) spaced apart by the gap 76 from the signal electrode 74 (e.g., a signal electrode plate or other conductive structure).

According to the illustrated embodiment, pressure sensor apparatus 30 and platform portion 21 may be inserted into electrode 15 such that the conductive electrode 15 surrounds pressure sensor apparatus 30. Further, FIG. 3A illustrates ground and supply contacts 81, 83 on the housing of the pressure sensor apparatus 30 electrically coupled, e.g., by laser ribbon bonds (LRB) 84, to respective conductive inserts 91, 92, respectively, integrated into lead body 11. Conductive inserts 91, 92 may have been incorporated into an insulative bulk of platform portion 21 via insert molding, or provided in any other manner.

Although not shown, at least in one embodiment, one of the plurality of conductors 13, such as shown in FIG. 1, which extends within lead body 11 from one of connectors 14, 16 is coupled to conductive insert 91, for grounding, and another of the plurality of conductors 13, extending from the same connector, is coupled to insert 92 as a supply. FIG. 3B further illustrates platform portion 21 including a by-pass lumen 65, which forms a passageway, alongside pressure sensor apparatus 30, in which another of the plurality of conductors 13 extends to electrically couple tip electrode 17 to the other of connectors 14, 16. In addition, FIG. 3B illustrates a conductive layer 62 forming a mounting surface for pressure sensor apparatus 30. According to one or more illustrative embodiments, conductive layer 62 may be grounded by a coupling with conductive insert 91, for example, via another laser ribbon bond, thereby providing additional shielding for one or more die and gap capacitor 32 of pressure sensor apparatus 30. Still further, FIG. 3B illustrates by-pass lumen 65 including a conductive liner 67 overlaid with an insulative layer 68 to isolate liner 67 from the conductor of the plurality of conductors 13 that extends within lumen 65 when the subassembly is integrated into lead body 11.

It will be recognized that various structures may be used to incorporate the pressure sensor apparatus 30 into a lead body, e.g., of an implantable medical electrical lead. For example, various structures may be used to provide for a ground connection electrically connectable to the pressure sensor apparatus, various structures may be used to provide for a supply connection electrically connectable to the pressure sensor apparatus, various structures may be used to mount the pressure sensor apparatus 30 within the lead, various structures may be used to provide for access to diaphragm electrode 72 such that the diaphragm electrode 72 deforms in response to a pressure applied thereto (e.g., pressure applied from tissue or fluids of a body), etc. Further, for example, as will be described herein, a pressure sensor apparatus may not need to be incorporated into a lead but may function apart from any such support structure, e.g., communicate pressure signals wirelessly.

Further, generally, the structure used to provide the capacitive pressure transducer, including the gap capacitor, of a pressure sensor apparatus suitable to provide reduced parasitic capacitance effects may vary as described herein. The illustrative pressure sensor apparatus 30 shown in FIGS. 1-3, which is further shown in FIGS. 4A-4C, shall be used to generally describe various manners for reducing such parasitic capacitance effects. Other variations thereof shall be discussed with respect to the other Figures provided herein.

Figure 4C:
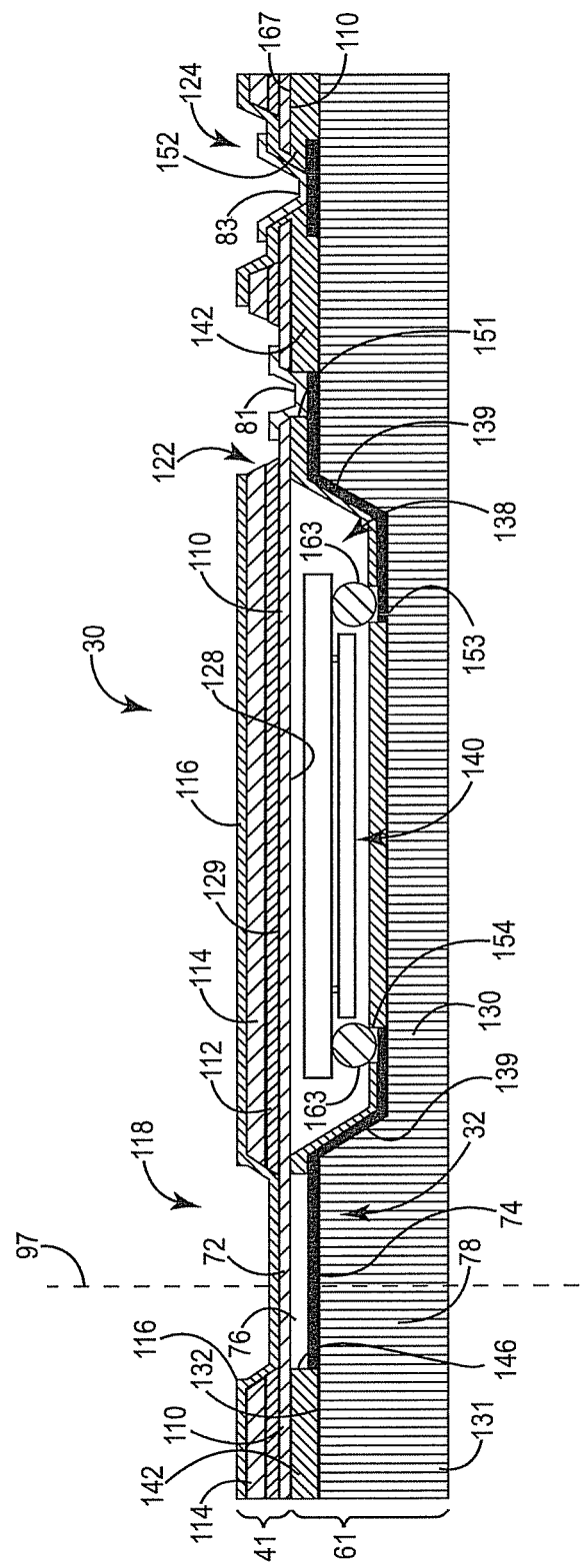
FIG. 4C is a cross-section view of the pressure sensor apparatus shown in FIG. 4A and FIG. 4B showing various portions thereof illustratively; some of which, but not necessarily all of which, lie along line C-C of FIG. 4A.

FIG. 4A is a perspective view of an exemplary pressure sensor apparatus 30. FIG. 4B is a cross-section perspective view of the pressure sensor apparatus 30 shown in FIG. 4A taken along line C-C thereof, and FIG. 4C is an illustrative cross-section view of the pressure sensor apparatus 30 shown in FIG. 4A and FIG. 4B showing various portions thereof illustratively; some of which, but not necessarily all of which, lie along line C-C of FIG. 4A. In other words, for simplicity purposes, FIG. 4C is not a true cross-section view along line C-C of FIG. 4A. For example, as will be apparent, thickness of layers are not provided to scale, the ground and supply contacts, as set forth below, are shown as being in the cross-section view, but do not both actually lie along line C-C of FIG. 4A, etc.

Generally, the pressure sensor apparatus 30 (e.g., which can be integrated into implantable lead 10) includes the first pressure sensor portion 41 including a diaphragm electrode 72 connectable to ground (e.g., via ground contact 81). The diaphragm electrode 72 is positioned in close proximity to the body when implanted therein such that the diaphragm electrode 72 is deformable in response to pressure applied thereto by the body. The pressure sensor apparatus 30 further includes the second pressure sensor portion 61 that includes the signal electrode 74. The first pressure sensor portion 41 and the second pressure sensor portion 61 are positioned relative to each other and coupled together (e.g., bonded to each other) to provide the gap 76 between the diaphragm electrode 72 and the signal electrode 74; thus, forming gap capacitor 32.

The second pressure sensor portion 61 further includes an insulator material 78 adjacent the signal electrode 74. As shown in FIG. 4C, the insulator material 78 is provided by a glass substrate which is also illustrated in FIG. 5B. However, as further described herein, such insulator material may be provided in one or more other manners using one or more other materials (e.g., a trench filled with an insulator material as illustratively shown in FIG. 5A, an opening through a silicon substrate filled with insulator material as shown in FIG. 6B, a molded glass substrate, a planar glass substrate having various portions thereof removed, such as with a blasting process, etc.). For example, a molded glass substrate may be formed by providing a mold and melting glass therein in a high temperature process. The signal electrode 74 is provided on and in direct contact with the insulator material 78 to electrically isolate the signal electrode 74 such that parasitic capacitance effects on the signal electrode 74 caused by electrical activity in the body when the pressure sensor apparatus 30 is implanted therein are reduced. Further, the diaphragm electrode 72 is grounded when the implantable pressure sensor apparatus 30 is implanted in the body to shield the signal electrode 72 from electrical activity (e.g., noise) in the body.

As shown in FIGS. 4A-4C, in one embodiment, the gap capacitor 32 is formed along an axis 97 when first pressure sensor portion 41 is bonded to second pressure sensor portion 61 (e.g., the diaphragm electrode 72 is centered along axis 97 with signal electrode 74 but separated by gap 76). In this illustrative embodiment, first pressure sensor portion 41 includes a silicon substrate 110, a portion of which provides the diaphragm electrode 72 (e.g., the diaphragm electrode itself being capable of being ground; such the silicon diaphragm electrode 72 provides both a deformation function and a grounding function). The silicon substrate (e.g., conductive substrate) extends between a first side surface 128 and a second side surface 129 opposite the first; with the first side surface 128 being adjacent the gap 76 of the gap capacitor 32. One or more layers may be formed thereon (e.g., patterned layers). For example, as shown in FIG. 4C, an oxide layer 112

(e.g., a thermal oxide layer) may be formed over the silicon substrate 110, and an additional layer of silicon 114 may be provided over the oxide layer 112. Still further, yet another oxide layer 116 (e.g., a silicon oxide) may be provided over one or more portions of the silicon layer 114.

One or more processes, such as deposition and patterning processes, may be used during the formation of the first pressure sensor portion 41, as well as other structure described herein in this and other embodiments, to provide one or more features (e.g., plasma etch processes, wet etch processes, photolithographic processes, sputtering deposition processes, vapor deposition processes, wafer bonding processes, chemical mechanical polishing or planarization processes, grinding processes, glass reflow processes, cleaning processes, etc.). For example, an opening or diaphragm window 118 may be formed in the silicon layer 114 to define the size of the diaphragm electrode 72. The diaphragm electrode 72 has a cross-sectional area orthogonal to the axis 97 and is generally deformable upon application of external pressure across this cross-sectional area, e.g., external pressure from one or more parts of the body when implanted therein. As shown in FIGS. 4A-4B, the shape of the diaphragm electrode 72 is generally rectangular. However, the diaphragm electrode may be of any shape, e.g., square, circular, elliptical, etc. In one embodiment, the oxide layer 112 may be used as a stop layer in the formation of the diaphragm window 118.

Further, for example, openings or windows 122, 124 may be defined in the silicon layers 110, 114 for use in forming ground contact 81 (e.g., ground/shield contact) as well as supply contact 83 (e.g., power/data contact). For example, the ground/shield contact may not only be connected to the diaphragm electrode as described herein, but also to one or more shielding components (e.g., braided wire layer in the lead) that serve to shield against noise. As shown in FIGS. 4A-4B, the openings 122, 124 are of a rectangular shape, however, such openings may also be any shape, e.g., square, circular, elliptical, etc.

The second pressure sensor portion 61 in this illustrative embodiment includes a glass substrate 130 to provide the insulator material 78, a portion of which provides a surface 132 on which signal electrode 74 is formed. The surface 132 lies opposite surface 131 of the glass substrate 130. Further, one or more metallization connections 139 (e.g., conductive traces) may also be formed thereon. The glass substrate 130 may be provided and/or formed in one or more manners, and one or more layers may be provided on the surface 132 thereof (e.g., patterned layers) to provide one or more features of the second pressure sensor portion 61.

For example, as shown in FIG. 4C, conductive material (e.g., gold) may be patterned on the glass substrate 130 to define the size of the signal electrode 74 (e.g., the electrode may be provided using any known formation process). The signal electrode 74 has a cross-sectional area orthogonal to the axis 97 and is formed on and in direct contact with the glass substrate 130. In FIG. 4A-4C, although not shown in its entirety, the shape of the signal electrode 74 is generally rectangular (much like diaphragm electrode 72). However, the signaling electrode may be of any shape, e.g., square, circular, elliptical, etc.

Further, in one embodiment, a recess may be provided in the glass substrate 130 to provide a cavity 138 between the first pressure sensor portion 41 and second pressure sensor portion 61 when coupled together. For example, such a recess may be provided as part of a molding process that may be used to provide the glass substrate 130 (e.g., using silicon as a micromold to create a glass shape), by removal of material from a planar glass substrate, etc. As described herein, one or more die 140 may be positioned or mounted in the cavity 138 to be electrically connected to at least the signal electrode 74.

Generally, the coupled first pressure sensor portion 41 and second pressure sensor portion 61 forming the cavity 138 (e.g., providing a housing for the pressure sensor apparatus) protect the die 140 in a hermetic cavity. Further, the housing provided by the coupled first pressure sensor portion 41 and second pressure sensor portion 61 also are configured to provide hermetic connections to the outside of the protective housing (e.g., ground and supply contacts 81, 83).

As described herein, one or more die 140 (e.g., one or more integrated circuit die or packages) may be positioned in the cavity 138. Such die may be used to provide any desired functionality, including that suitable for measuring pressure. For example, the one or more die 140 may include analog/digital integrated circuits that provide signal conditioning functions (e.g., filtering and amplification), signal processing functions, logic functions, etc. Further, such die may include memory (e.g., volatile/non-volatile) that stores programs used by the integrated circuits to provide the functions associated with the integrated circuits. Further, such memory may store measured parameters, e.g., measured pressures.

Further, for example, such integrated circuits 140 for use in connection to gap capacitor 32 may include application specific integrated circuits (ASICS), microprocessors, operation amplifiers, timing oscillators, capacitor arrays, or any other die that may be beneficial for use in the pressure sensor apparatus 30. Such die may be stacked and interconnected using wirebonds (e.g., such stacked/wirebonded die or ICs may define the "z" dimension of the die cavity 138 inside of the MEMS housing or package); wirebonds may be used to connect the die to contacts, the length and width of the largest die or integrated circuit may define the minimum size of the inside length and width of the MEMS housing; and the width of the widest die or IC may define the maximum width of the capacitor electrodes such as the signal electrode 74 or diaphragm electrode 72.

Still further, for example, as shown in FIG. 4C, the patterning of the conductive material (e.g., gold), such as described for forming signal electrode 74, may also provide metallization connections 139 for electrically connecting various components of the pressure sensor apparatus 30. For example, such metallization connections 139 may be used for electrically connecting the signal electrode 74 to one or more die 140 in cavity 138, may be used for electrically connecting the one or more die 140 to ground contact 81, may be used for electrically connecting the one or more die 140 to supply contact 83, etc.

In other words, as shown in FIG. 4C, the signal electrode 74 is provided on and in direct contact with the glass substrate 130 and electrically connected to one or more die 140 of the pressure sensor apparatus 30 via conductive material (e.g., metallization connections 139) patterned on at least a portion of the glass substrate 130. As such, one or more metallization connections 139 are provided between the signal electrode 74 and the die cavity 138 for connection of the signal electrode 74 to one or more die 140 positioned in the die cavity 138. With the one or more metallization connections 139 being formed on the glass substrate 130, such the metallization connections 139 are also electrically isolated such that parasitic capacitance effects on the one or more metallization connections 139 caused by electrical activity in the body when the pressure sensor apparatus is implanted therein are also reduced.

Further, for example, an oxide layer 142 (e.g., silicon oxide, silox, etc.) may be patterned over the glass substrate 130 and patterned conductive material (e.g., connections 139). For example, to provide gap 76 having a gap distance between the diaphragm electrode 72 and signal electrode 74, an opening 146 may be defined by such patterning (e.g., the thickness of the silicon oxide layer may be used to control the gap distance; the distance along axis 97 between the diaphragm electrode 72 and the signal electrode 74). Still further, for example, although not shown, the gap 76 having a gap distance between the diaphragm electrode 72 and signal electrode 74 may also be provided, at least in part, by forming a recess in the insulator material 78, e.g., the glass substrate 130, in which or on which the signal electrode 74 may be formed.

Still further, one or more other openings may be defined by such patterning to provide for access to conductive material (e.g., patterned metallization connections 139) for electrical connection of various elements of the pressure sensor apparatus 30. For example, openings 151, 152 may be defined in the oxide layer 142 for use in forming ground contact 81 (e.g., ground/shield contact) as well as supply contact 83 (e.g., power/data contact). Still further, one or more openings 153, 154 may be defined for use in connection of one or more die within the cavity 138, e.g., via solder balls 163.

FIG. 4C illustrates gap capacitor 132 coupled to the one or more die 140 (e.g., one or more integrated circuits) positioned in cavity 138 via metallization connections 139 (e.g., conductive traces). Further, such metallization connections 139 also may couple the one or more die 140 to ground contact 81 and to supply contact 83 (connection not shown).

The diaphragm electrode 72 is in contact with ground within the in-vivo environment to shield the signal electrode 74 from noise (e.g., noise due to the electrical activity within the body in which the pressure sensor apparatus 30 is implanted). The diaphragm electrode 72 may be connected to ground potential through the electrical connection of the diaphragm electrode 72 (e.g., formed by part of silicon layer 110) to the ground contact 81 (e.g., the silicon layer 110 extending over cavity 138 and connecting to ground contact 81 on the side of the cavity 138 opposite the diaphragm electrode 72); the ground contact 81 being coupled to ground through connection to the ground contact 91 of the lead 10 (e.g., through connection of the lead to an implanted device). In one embodiment, the silicon layer 110 which provides the diaphragm electrode 72 functions as a ground plane (e.g., in the same manner as a ground plane found in multilayer circuit boards). However, the diaphragm electrode may be connected to ground potential by any other manner. For example, the diaphragm electrode may be connected to a ground contact that is located on the packaged pressure sensor apparatus that is in direct contact with body tissue or fluids when implanted (e.g., such as shown in the wireless device of FIGS. 7A-7C).

In one or more embodiments, the diaphragm electrode 72 may be in contact with the body in which it is implanted (e.g., by contact with body tissue or fluids). In other words, in one embodiment, the diaphragm electrode 72 need not be insulated from the body by the oxide layer 112 shown in FIG. 4C.

Generally, as presented herein to reduce parasitic capacitance and noise, the signal electrode is shielded from noise by the grounded diaphragm electrode (e.g., located above the signal electrode and between the signal electrode and the body when implanted therein), and the signal electrode is also isolated by insulator material (e.g., located below the signal electrode) on which it is directly provided (e.g., formed, deposited, patterned, etc.). The insulator material (e.g., borosilicate glass (BSG) such as Borofloat 33, or some other biostable insulator such as silica, or ceramic) electrically isolates the signal electrode such that parasitic capacitance effects on the signal electrode caused by electrical activity in the body when the pressure sensor apparatus is implanted therein are reduced.

One will recognize, for example, that when nominal sensor capacitance is on the order of 1 pF, parasitic capacitance can easily appear and affect the sensitivity of the sensor, especially when one of the capacitor electrodes of the gap capacitor must be in close contact with body tissues or fluids (e.g., which is the case when the pressure sensor apparatus is implanted within a body or held in close contact therewith). The environment (e.g., in-vivo or implantable environment), the sensor materials (e.g., such as the insulator material used to isolate the signal electrode), and their relative configurations (e.g., holding the diaphragm electrode which is closer to the body than the signal electrode at ground potential), all play a role in achieving an effective pressure sensor apparatus with reduced parasitic capacitance effects.

For the insulating material to be effective in isolating the signal electrode it must be of sufficient thickness and bulk resistance to reduce parasitic capacitance (e.g., maximize the sensitivity of the gap capacitor). The following mathematical foundation sets forth an approximation using various assumptions for use in the design of at least one embodiment of a pressure sensor apparatus (e.g., having a rectangular shaped gap capacitor).

Generally there are four geometries available for manipulation to achieve the specifications of a pressure sensor apparatus having such a shaped capacitor. These four geometries are: (1) Diaphragm area: Length (L), Width (l); (2) Diaphragm thickness (t); (3) Cavity depth or gap (g); (4) Capacitor plate area: length (x) and width (y). (Note: In one embodiment, a final offset adjustment may be possible by manipulation of the pressure inside of the sealed cavity.)

There are two governing equations for this microstructure:

$$d = \frac{0.0284 \cdot W}{Et^3 \left( \frac{L}{l^3} + \frac{1.056 \cdot l^2}{L^4} \right)} \quad \text{(Eqn. 1)}$$

$$C = \frac{\varepsilon A}{g} \quad \text{(Eqn. 2)}$$

Equation 1 is the formula to calculate the deflection of the center of a rectangular plate with fixed edges and a uniformly distributed pressure over the diaphragm. Equation 2 is the formula for calculating the capacitance between two conductive plates. The capacitor is defined by the diaphragm as one electrode and the metal plate in the cavity as the other electrode.

The definitions for the parameters in the equations above are:

{g} is the distance between the plates (gap) or cavity depth. (cm)
{d} is the deflection of the diaphragm (one of the plates). (mm)
{p} is the applied pressure. (Newtons/mm$^2$)
{W} is the applied load. (Newtons)
{L} is the long edge of the diaphragm. (mm)
{l} is the shortest edge of the diaphragm. (mm)
{E} is Young's modulus for silica. (Newtons/mm$^2$)
{t} is the diaphragm thickness. (mm)
{C} is Capacitance measured across two plates. (Farads)
{∈} is the permittivity of the dielectric between the plates. (F/cm)
{A} is the Area of the capacitor plates. (cm$^2$)
{x} is the length of the capacitor plates. (cm)
{y} is the width of the capacitor plates. (cm)

Equation 1 provides a boundary for the diaphragm size and thickness. At the maximum specified pressure one generally does not allow (d) to be larger than the cavity depth (g), or the diaphragm will hit the bottom of the cavity (although such contact with the bottom of the cavity may be acceptable depending on the desired sensitivity to be achieved; such contact would likely reduce sensitivity as the diaphragm flattens out on the bottom of the cavity). The length and thickness of the diaphragm must be chosen to prevent this, yet still provide the needed sensitivity. At any given pressure the gap decreases by an amount equal to the deflection (as a first order approximation). So the new gap will be equal to (g-d):

$$C = \frac{\varepsilon A}{g - d/10} \quad \text{(Eqn. 3)}$$

"d" is divided by 10 to get the deflection units into cm.

$$W = p \cdot L \cdot l \quad \text{(Eqn. 4)}$$

The applied load on the diaphragm (W) is equal to the pressure x area of the diaphragm.

Substituting Eqn. 4 into Eqn. 1 results in:

$$d = \frac{0.0284 \cdot p \cdot L \cdot l}{Et^3 \left( \frac{L}{l^3} + \frac{1.056 \cdot l^2}{L^4} \right)} \quad \text{(Eqn. 5)}$$

Now one can combine Eqn. 3 and 5:

$$C = \frac{\varepsilon A}{g - \dfrac{0.00284 \cdot p \cdot L \cdot l}{Et^3 \left( \frac{L}{l^3} + \frac{1.056 \cdot l^2}{L^4} \right)}} \quad \text{(Eqn. 6)}$$

The area of the capacitor is defined by x and y (one can also simplify the denominator).

$$C = \frac{\varepsilon \cdot x \cdot y}{g - \dfrac{0.00284 \cdot p}{Et^3 \left( \frac{L}{l^4} + \frac{1.056 \cdot l}{L^5} \right)}} \quad \text{(Eqn. 7)}$$

Equation 7 describes the behavior of the sensor capacitor under pressure. Note that pressure (p) is a differential pressure. For example, if the cavity is backfilled to 300 mmHg, then at room pressure (750 mmHg), one will have a pressure of 450 mmHg on the diaphragm. An important assumption in this equation is that the deflection is small, and thus the deflection produces a uniform change in gap. The deflected plate is also assumed to be flat. This isn't true, of course, since a given uniform pressure causes only the center point to deflect the full distance defined by the equations. For small deflections, however, this is a good first approximation.

Some constants and useful relationships are provided: 1 Newton/mm$^2$=7500.6156 mmHg; $E_{silicon}$=165 GPa=165000 Newtons/mm$^2$; $\varepsilon_0$=8.854188×10$^{-14}$ F/cm; $\varepsilon_r$=1.

For example, using such mathematical foundation, an exemplary capacitive sensor with a value of 1 pf at 750 mmHg can be designed. For example, the signal electrode may have a parasitic capacitance 10 times less than the sensor capacitance (i.e., less than 0.1 pf) to increase sensitivity. The signal electrode must be isolated by being directly formed on and in contact with the insulator material. If one assumes the insulator material is glass (e.g., BSG) with a permittivity of 3.2, then the thickness of the insulator material should be greater than 32 times the sensor gap distance or depth. For example, if the gap design is 4 um, therefore, the insulator material under the signal electrode should be greater than 128 um or approximately 5 mils. For example, the sensitivity of the sensor may be greater than 63 ppm/mmHg.

With further reference to FIG. 4C, in one embodiment, the diaphragm electrode 72 of the first pressure sensor portion 41 lies parallel to the signal electrode 74 of the second pressure sensor portion 61 along axis 97 of gap capacitor 32 formed thereby (e.g., each electrode being centered on the axis 97). As described herein, the diaphragm electrode 72 is deformable over a cross-sectional area orthogonal to the axis 97. Further, the signal electrode 74 which is provided on and in direct contact with the insulator material 78 has a cross-sectional area orthogonal to the axis 97 that is about the same as, or no more than 95 percent smaller than, the deformable cross-sectional area of the diaphragm electrode 72 orthogonal to the axis. Further, in one or more embodiments, the signal electrode 74 has a cross-sectional area orthogonal to the axis 97 that is about the same as, or no more than 50 percent smaller than, the deformable cross-sectional area of the diaphragm electrode 72 orthogonal to the axis. Further, in one or more embodiments, the signal electrode 74 has a cross-sectional area orthogonal to the axis 97 that is about the same as, or no more than 30 percent smaller than, the deformable cross-sectional area of the diaphragm electrode 72 orthogonal to the axis. Still further, in one or more embodiments, the signal electrode 74 has a cross-sectional area orthogonal to the axis 97 that is about the same as, or no more than 20 percent smaller than (and in many cases no more than 10 percent smaller than), the deformable cross-sectional area of the diaphragm electrode 72 orthogonal to the axis.

Also, as discussed herein, the signal electrode 72 is provided on and in direct contact with the insulator material 78 of the second pressure sensor portion 61 to electrically isolate the signal electrode such that parasitic capacitance effects are reduced. In one or more embodiments, the signal electrode 72 is isolated such that the parasitic capacitance of the signal electrode 72 when the pressure sensor apparatus 30 is implanted within the body is less than 0.5 times a capacitance of the gap capacitor 32 formed by the diaphragm electrode 72 separated from the signal electrode 74 by the gap 76. Further, in one or more embodiments, the signal electrode 72 is isolated such that the parasitic capacitance of the signal electrode 72 when the pressure sensor apparatus 30 is implanted within the body is less than 0.1 times a capacitance of the gap capacitor 32 formed by the diaphragm electrode 72 separated from the signal electrode 74 by the gap 76. Still further, in one or more embodiments, the signal electrode 72 is isolated such that the parasitic capacitance of the signal electrode 72 when the pressure sensor apparatus 30 is implanted within the body is less than 0.01 times a capacitance of the gap capacitor 32 formed by the diaphragm electrode 72 separated from the signal electrode 74 by the gap 76.

As recognized from the mathematical formulation, depending on the permittivity of the insulator material 78 and the sensitivity desired for the pressure sensor apparatus 30, the insulator material 78 should be of a particular thickness below the signal electrode 72. In one or more embodiments, when the insulator material 78 is a glass insulator material (e.g., BSG), the glass insulator material has a thickness adjacent the signal electrode 72 that is greater than about 6 times the gap distance separating the diaphragm electrode 72 from the signal electrode 74. In one or more other embodiments, the insulator material may have a thickness that is greater than about 32 times the gap distance, and even greater than about 320 times the gap distance.

As described herein, to form the pressure sensor apparatus 30, the first pressure sensor portion 41 and the second pressure sensor portion 61 are coupled together. For example, in one or more embodiments, the connection surfaces (e.g., surface 128 of silicon substrate 110 and upper surface 167 of oxide layer 142) of such portions 41, 61, respectively, may be coupled together (e.g., using plasma-enhanced bonding) to assemble the pressure sensor apparatus 30 and to form an interface therebetween. In one or more embodiments, bonding the first and second pressure sensor portions 41, 61 together to assemble the pressure sensor apparatus 30 may be implemented using any wafer and/or die bonding process (e.g., bonding a wafer including the first pressure sensor portions with a wafer including the second pressure sensor portions, which also refers to the bonding of an individual die to a full wafer and the bonding of an individual die to another individual die), such as chemical bonding processes (e.g., those using adhesion promoters, etc.), high temperature bonding processes (e.g., thermal fusion bonding, etc.), hydrogen bonding processes, anodic bonding processes, and oxide bonding processes (e.g., plasma enhanced bonding, etc.). For example, when the diaphragm electrode 72 and the signal electrode 74 are aligned along axis 97, bonding may be performed to form the packaged device, e.g., providing a hermetically sealed housing or package for the pressure sensor apparatus 30. Further, for example such bonding may be performed using one or more of the processes described in U.S. Provisional Application No. 61/406,961, filed 26 Oct. 2010, and entitled "Wafer-Scale Package Including Power Source" which is incorporated in its entirety herein.

As described in at least one embodiment herein, a hermetically sealed pressure sensor apparatus 30 is provided as a packaged device (e.g., a pressure sensor including various electronic components housed within a package fabricated using multiple substrates). In at least one embodiment, fabrication of the packaged devices includes providing various components and layers relative to one of the substrates, then coupling them together such that the various components are housed within one or more cavities defined thereby, and/or one or more devices are formed upon coupling (e.g., formation of gap capacitor 32).

In one or more embodiments, a pressure sensor apparatus as described herein (e.g., provided as a packaged device) may include a variety of different electrical components in combination with the gap capacitor 32. In one example, the pressure sensor apparatus may include one or more integrated circuits. Integrated circuits may be fabricated on one or more integrated circuit die (e.g., silicon or glass) that are subsequently mounted in the pressure sensor apparatus (e.g., mounted in cavity 138). Additionally, or alternatively, the pressure sensor apparatus may include integrated circuits fabricated directly onto one or more substrates, e.g., embedded within or deposited onto the substrates.

In one or more embodiments, the pressure sensor apparatus may include components used for communication with devices external thereto. For example, the pressure sensor apparatus may include an antenna. The antenna may be fabricated on a die (e.g., glass or semiconductor) that is mounted within the apparatus. Alternatively, or additionally, the antenna may be fabricated on one of the substrates of the apparatus. Alternatively, or additionally, the antenna may be fabricated as a wirewound coil and mounted on one of the substrates within the package.

In some examples, the pressure sensor apparatus may include passive components, e.g., integrated or discrete passive components, such as resistors, capacitors, inductors, etc. Additionally, as described herein, the pressure sensor apparatus includes at least one MEMS component in the form of a gap capacitor including a diaphragm electrode and a signaling electrode separated by a gap.

Further, as described herein, the pressure sensor apparatus may also include conductive traces that interconnect components included in the pressure sensor apparatus and that interface these components to devices external thereto. For example, the pressure sensor apparatus may include one or more layers of conductive traces that are deposited on or within substrates to provide metallization connections.

The pressure sensor apparatus may also include one or more vias that extend from an inside of the pressure sensor apparatus, through one or more substrates, to an outside surface of the pressure sensor apparatus. In one example, the components of the pressure sensor apparatus may communicate using intrabody communication (e.g., tissue conductance communication) to other devices located on or within the patient through contacts or electrodes connected to such vias (e.g., see, for example, the wireless device of FIGS. 7A-7C).

Further, in one or more embodiments, the pressure sensor apparatus 30 may include contacts, bonding pads, or other features used for electrically interconnecting one or more components of the apparatus. Such interconnections may include use of conductive materials, e.g., metals, such as copper, aluminum, titanium, platinum, gold, and nickel. For example, conductive traces used for interconnection purposes may include conductive materials, e.g., metals, such as copper, aluminum, titanium, platinum, tungsten, gold, nickel, or any other conductor suitable for electrically connecting components of pressure sensor apparatus. In some examples, one or more external contacts may include conductive materials, e.g., metals, such as titanium, platinum, gold, niobium, or alloys of these materials. Yet further, in some examples, when the apparatus is configured to be implanted in a patient, external contacts may include a biocompatible material such as titanium, platinum, gold, niobium, or alloys of these materials. Additionally, or alternatively, external contacts may include tantalum and/or alloys of tantalum.

Components of the pressure sensor apparatus 30 may be electrically coupled to other components thereof (or other interconnections) via various methods. For example, methods such as solder techniques (e.g., use of solder bumps attached to bonding pads of a components), thermo-compression stud bumping, conductive adhesives, anisotropically formed conductive films, tape automated bonding, laser ribbon bonding, and wire bonding, may be used.

In some examples, the pressure sensor apparatus may be implanted in a patient or attached externally to a patient. When the pressure sensor apparatus is configured to be implanted in the body of a patient, the pressure sensor apparatus may include an exterior coating that enhances biocompatibility of the pressure sensor apparatus for implantation, e.g., provides a greater biocompatibility than the materials used to form the pressure sensor apparatus portions bonded together (e.g., glass or silicon). For example, the exterior coating may include a titanium coating that covers the outside of the pressure sensor apparatus, excluding any electrodes or other electrical contacts that are external to the pressure sensor apparatus. In another example, the exterior coating may include a silicone layer that covers the outside of the pressure sensor apparatus, excluding any electrodes or other electrical contacts that are external to the pressure sensor apparatus (e.g., ground contacts such as when the diaphragm electrode 72 is held at ground potential).

FIG. 4C illustrates a cross-sectional side view of the pressure sensor apparatus 30 that includes first pressure sensor portion 41 and second pressure sensor portion 61, with the second pressure sensor portion 61 including recesses (e.g., recesses or openings defined in the substrate itself or defined by patterned layers on the substrate) for use in forming gaps (e.g., the gap of gap capacitor 32), cavities (e.g., cavity 138), etc. However, for example, the pressure sensor apparatus may include substrates and layers foamed thereon having different geometries so long as various components may be housed within one or more cavities foamed between the separate substrates, and the features provided in the pressure sensor apparatus 30 (e.g., gap capacitor 32, interconnections, contacts, etc.) are foamed. For example, both portions 41, 61 included in the pressure sensor apparatus 30 may each define recessed portions that enclose components thereof.

Further, for example, instead of second pressure sensor portion 61 including one or more recesses for use in forming gaps (e.g., the gap of gap capacitor 32), cavities (e.g., cavity 138), etc., the first pressure sensor portion 41 may define recesses (e.g., recesses or openings defined in the substrate itself or defined by patterned layers on the substrate) for use in forming gaps (e.g., the gap of gap capacitor 32), cavities (e.g., cavity 138), etc. Further, additionally or in the alternative, both the first and second pressure sensor portion 41, 61 may include one or more recesses for use in forming gaps (e.g., the gap of gap capacitor 32), cavities (e.g., cavity 138), etc. when coupled.

Although the pressure sensor apparatus 30 portion is illustrated as including a single cavity 138 and a single gap capacitor 32 formed between the first and second pressure sensor portions 41, 61, multiple cavities may be formed using multiple substrates or portions formed therefrom, bonded to a single supporting substrate. For example, the pressure sensor apparatus 30 may include a single second pressure sensor portion 61, with multiple capping first pressure sensor portions that are bonded together to form the apparatus (e.g., one for use in forming the gap capacitor and one to form cavity 138, or even more to faun additional features or cavities).

The first pressure sensor portion 41 and the second pressure sensor portion 61 may include or be formed of a variety of materials. For example, first pressure sensor portion 41 may include, but is not limited to the use of semiconductor materials such as, silicon substrates and/or silicon carbide substrates, or any other suitable conductive material that may be used to form groundable diaphragm electrode 72. Second pressure sensor portion 61 may include glass substrates, such as borosilicate glass (BSG), sapphire, ceramic, or fused silica; may include semiconductor substrate materials that include one or more regions thereof that are formed of an insulating material such as glass insulator material (such as borosilicate glass (BSG), sapphire, ceramic, or fused silica, upon which the signal electrode 74 may be foamed); as well as any other insulating materials suitable to isolate the signal electrode 74 to reduce parasitic capacitance effects.

Figure 5A:
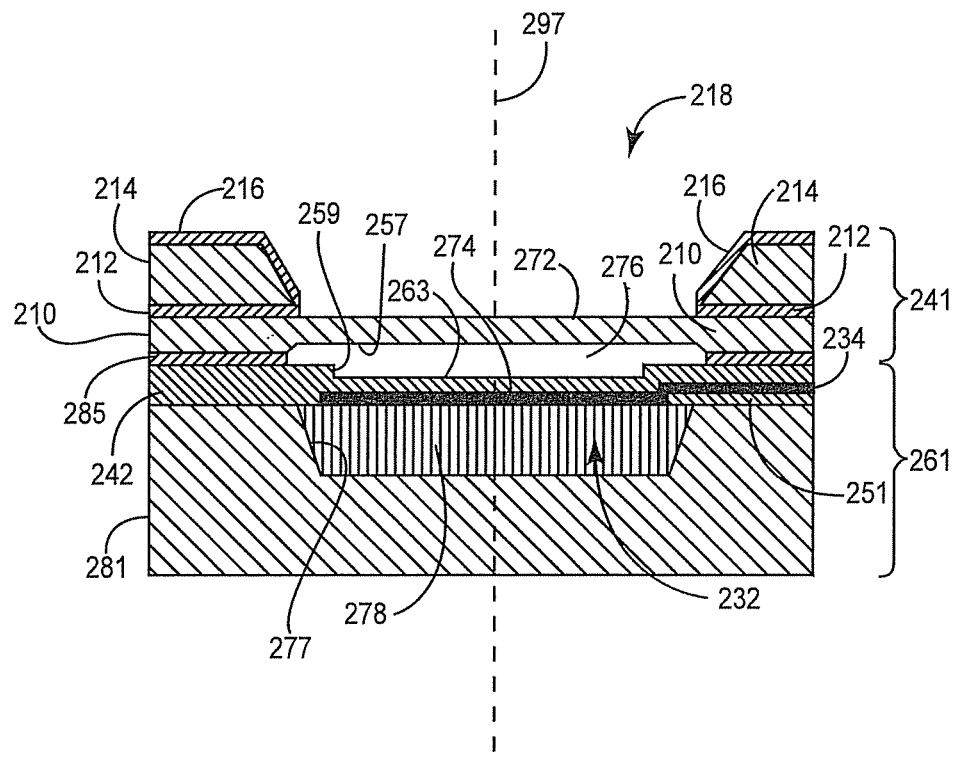
FIG. 5A is an illustrative cross-section view of one embodiment of a portion of a pressure sensor apparatus including a gap capacitor.
Figure 5B:
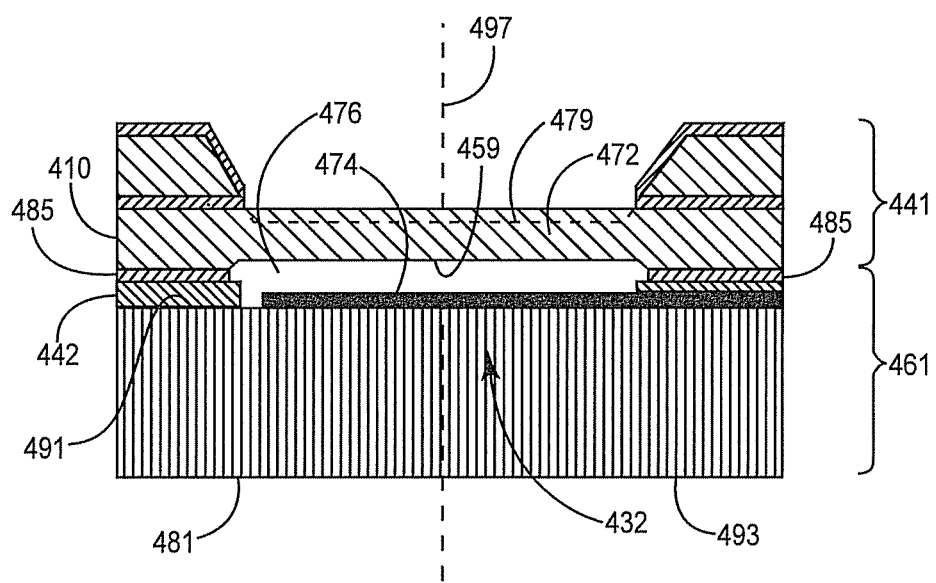
FIG. 5B is an illustrative cross-section view of another embodiment of a portion of a pressure sensor apparatus including a gap capacitor.
Figure 6A:
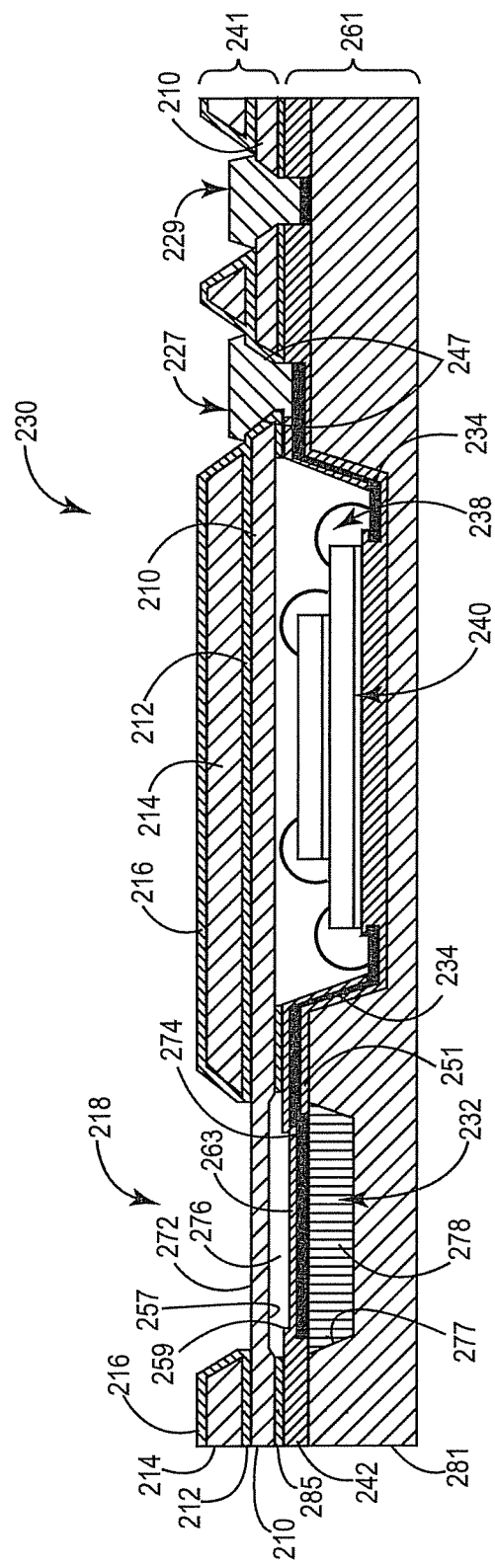
FIG. 6A is an illustrative cross-section view of another embodiment of a pressure sensor apparatus including a gap capacitor similar to that shown in FIG. 5A.
Figure 6B:
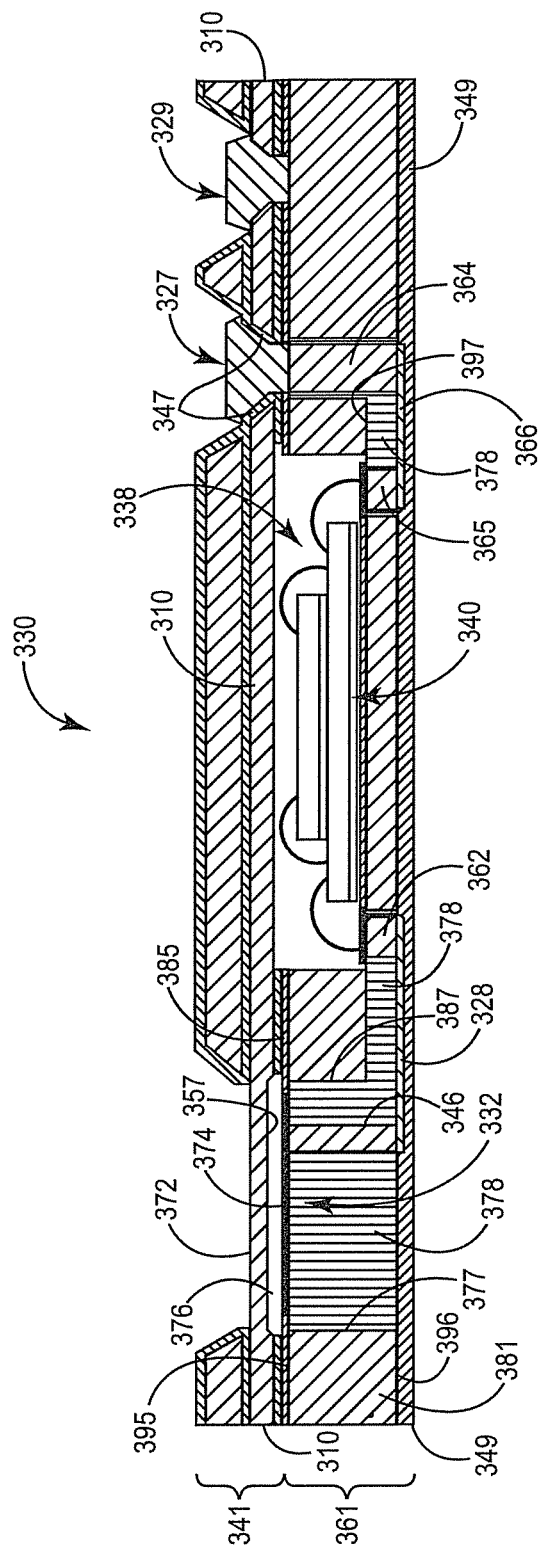
FIG. 6B is an illustrative cross-section view of another embodiment of a pressure sensor apparatus.

FIG. 5A is an illustrative cross-section view of an alternate embodiment of a portion of a capacitive pressure sensor apparatus 230 (such as shown in FIG. 6A) including a gap capacitor 232. For example, as shown in FIG. 5A, the insulator material 278 on which signal electrode 274 is entirely provided is of a particular thickness within a recess 277 defined in a substrate (e.g., a planar silicon substrate), as opposed to an insulator substrate being used as shown in FIG. 4C.

In other words, for example, as shown in FIG. 5A, the pressure sensor apparatus 230 includes a first pressure sensor portion 241 including a diaphragm electrode 272 connectable to ground. The diaphragm electrode 272 is positioned in close proximity to the body when implanted therein such that the diaphragm electrode 272 is deformable in response to pressure applied thereto by the body. The pressure sensor apparatus 230 further includes second pressure sensor portion 261 that includes signal electrode 274. The first pressure sensor portion 241 and the second pressure sensor portion 261 are coupled to each other (e.g., bonded to each other) to provide the gap 276 between the diaphragm electrode 272 and the signal electrode 274; forming gap capacitor 232.

The second pressure sensor portion 261 includes a planar substrate 281 having a recess or trench 277 defined therein. For example, the trench or recess 277 may be defined in, for example, a silicon substrate, using any known formation process (e.g., a plasma etch process). The trench or recess 277 is then filled with the insulator material 278. For example, a glass insulator material, such as borosilicate glass (BSG), sapphire, or fused silica, may be used to fill the trench 277. Any process of providing such a glass insulator material in the trench or recess 277 may be used, such as, for example, a high temperature process that melts the glass insulator material for filling the trench 277.

The signal electrode 274 is provided on and in direct contact with the insulator material 278 such that the insulator material 278 electrically isolates the signal electrode 274. As described herein, the thickness of the insulator material 278 must be sufficient to reduce the parasitic capacitance effects on the signal electrode 274 caused by electrical activity in the body when the pressure sensor apparatus 230 is implanted therein. The signal electrode 274 may be formed by any known conductive material formation process (e.g., a patterning process, using one or more deposition processes, such as sputtering or chemical vapor deposition).

One or more layers 242 may be provided on the surface of substrate 281 (e.g., patterned layers) to provide one or more features of the second pressure sensor portion 261. The second pressure sensor portion 261 in this illustrative embodiment may further include one or more metallization connections 234 (e.g., conductive traces). For example, such conductive traces 234 (e.g., metallization connections for connecting the signal electrode 274 to one or more die such as shown in FIG. 4C) are insulated from silicon substrate 281 by oxide layer 251 formed thereon. Further, for example, one or more patterned metal layer or layers may be used to define the size of the signal electrode 274 (e.g., may be patterned using any patterning processes, such as photolithographic patterning processes followed by an etch process). Further, one or more patterned layers may be used to create a recess 259 along axis 297 for use in forming gap 276 between the signal electrode 274 and diaphragm electrode 272 (e.g., when the pressure sensor portions are coupled, the recess 259 of the second pressure sensor portion 261 faces towards the first pressure sensor portion 241). Still further, oxide material 263 may be provided over the signal electrode 274 to prevent any possible short between the capacitor electrodes 272, 274 if, for example, deformation of the diaphragm electrode 272 exceeds the gap distance. Still further, one or more other material layers (e.g., oxide layer, adhesion layer, etc.) such as patterned layer 285 may be used, for example, to promote adhesion in a particular bonding process, to increase the gap distance between the signal electrode 274 and diaphragm electrode 272, etc.

As shown in FIG. 5A, in one embodiment, the gap capacitor 232 is formed along axis 297 when first pressure sensor portion 241 is bonded to second pressure sensor portion 261 (e.g., the diaphragm electrode 272 is centered along axis 297 with the signal electrode 274 but separated by gap 276). In this illustrative embodiment, the first pressure sensor portion 241 is formed of a silicon substrate 210, a portion of which provides the diaphragm electrode 272. One or more layers are formed on the silicon substrate 210 (e.g., patterned layers). For example, as shown in FIG. 5A, an oxide layer 212 (e.g., a thermal oxide layer) may be formed over the silicon substrate 210, and an additional layer of silicon 214 may be provided over the oxide layer 212. Thereafter, yet another oxide layer 216 (e.g., a thermal oxide layer) may be formed over one or more portions of the silicon layer 214. One or more patterning processes may be used during the formation of the first pressure sensor portion 241 to provide one or more features thereof. For example, opening or diaphragm window 218 may be formed in the silicon layer 214 to define the size of the diaphragm electrode 272, in a manner such as described with reference to FIG. 4C, such that the diaphragm electrode is deformable upon application of external pressure thereto, e.g., external pressure from one or more parts of the body when implanted therein. The opening 218 may be formed using any known material removal process (e.g., a plasma etching process or wet etching process).

Further, for example, a recess 257 may be defined in the silicon layer 214 along axis 297 for use in forming gap 276 between the signal electrode 274 and diaphragm electrode 272 (e.g., when the pressure sensor portions are coupled, the recess 257 of the first pressure sensor portion 241 faces towards the second sensor portion 261). For example, any known silicon etch process may be used to define such a recess 257.

The gap capacitor 232 of FIG. 5A is further shown in FIG. 6A with the diaphragm electrode 274 electrically connected to ground contact 229 as part of pressure sensor apparatus 230. Silicon substrate 210 is connected to ground contact 229, while contact 227 is electrically insulated therefrom by one or more insulator materials 247 (e.g., thermal oxide or deposited oxide). Further, as shown therein, metallization connections 234 (e.g., conductive traces) formed on top of substrate 281, but electrically insulated therefrom, connect the signal electrode 274 to one or more die 240 in cavity 238.

In one or more embodiments, the trench of the second pressure sensor portion to be provided or filled with insulator material may be formed through an entire thickness of the substrate as shown in FIG. 6B. For example, as shown in FIG. 6B, pressure sensor apparatus 330 includes a first pressure sensor portion 341 including a diaphragm electrode 372 connected to ground contact 329. The diaphragm electrode 372 is positioned in close proximity to the body when implanted therein such that the diaphragm electrode 372 is deformable in response to pressure applied thereto by the body. The pressure sensor apparatus 330 further includes second pressure sensor portion 361 that includes signal electrode 374. The first pressure sensor portion 341 and the second pressure sensor portion 361 are coupled to each other (e.g., bonded to each other) to provide the gap 376 between the diaphragm electrode 372 and the signal electrode 374, and as such form gap capacitor 332.

The second pressure sensor portion 361 includes a planar substrate 381 having one or more openings formed therethrough and/or therein, e.g., openings 377, 387, 397. For example, such openings may be defined in, for example, a silicon substrate, (e.g., an opening may extend from a first substrate surface 395 to second substrate surface 396 lying opposite the first substrate surface 395) using any known formation process (e.g., an anisotropic plasma etch process, a back side etch process, etc.). The openings are filled with insulator material 378. For example, a glass insulator material, such as borosilicate glass (BSG), sapphire, or fused silica, may be used to fill the openings (e.g., using a high temperature process that melts the glass insulator material to fill the opening or openings).

The signal electrode 374 is provided on and in direct contact with the insulator material 378 filling opening 377 and 387 such that the insulator material 378 electrically isolates the signal electrode 374 in a manner to reduce the parasitic capacitance effects on the signal electrode 374 caused by electrical activity in the body when the pressure sensor apparatus 330 is implanted therein. A silicon feedthrough 346 surrounded by the insulator material (e.g., glass insulator material) is provided for use in connection of the signal electrode 374 to one or more die 340 in cavity 338. Other silicon feedthroughs are formed in the second pressure sensor portion 361 to provide connection of components thereof. For example, the signal electrode 374 is connected to the one or more die 340 in cavity 338 via feedthrough 346 which is connected to silicon feedthrough 362 via conductive trace 328 (e.g., conductive trace 328 having an oxide layer 349 formed thereon). Further, for example, silicon feedthroughs 364 and 365 are connected by conductive trace 366 (e.g., conductive trace 366 having oxide layer 349 formed thereon) to provide connection between supply contact 327 and one or more die 340. It is noted that the silicon feedthroughs are surrounded by insulator material (e.g., glass insulator material) and that the entire area under the signal electrode 374 is insulator material as well (except for the connection of the signal electrode 374 to the silicon feedthrough 346).

As further shown in FIG. 6B, the first pressure sensor portion 341 is similar to the first pressure sensor portion 241 shown in FIGS. 5A and 6A. Therefore, it will not be described in any further detail, except to note that recess 357 defined in the silicon layer 310 along axis 297 is primarily responsible for forming gap 376 between the signal electrode 374 and diaphragm electrode 372. However, one or more other material layers (e.g., oxide layer, adhesion layer, etc.) such as patterned layer 385 may be used, for example, to promote adhesion in a particular bonding process, to increase the gap distance between the signal electrode 374 and diaphragm electrode 372, etc.

The gap capacitor 332 of FIG. 6B is shown with the diaphragm electrode 374 electrically connected to ground contact 329 of pressure sensor apparatus 330. Silicon substrate 310 is connected to ground contact 329, while contact 327 is electrically insulated therefrom by one or more insulator materials 347.

FIG. 5B is an illustrative cross-section view of an alternate embodiment of a portion of a capacitive pressure sensor apparatus including a gap capacitor 432. For example, as shown in FIG. 5B, the insulator material on which signal electrode 474 is provided is a glass substrate 481 similar to the insulator substrate described with reference to FIG. 4C. The glass substrate material extends from a first side surface 491 to a second side surface 493 opposite the first side surface 491. The signal electrode 474 is provided on and in direct contact with the first side surface 491 of the glass substrate 481.

In other words, for example, as shown in FIG. 5B, the pressure sensor apparatus includes a first pressure sensor portion 441 including a diaphragm electrode 472 connectable to ground. The diaphragm electrode 472 is positioned in close proximity to the body when implanted therein such that the diaphragm electrode 472 is deformable in response to pressure applied thereto by the body. The pressure sensor apparatus further includes second pressure sensor portion 461 that includes signal electrode 474. The first pressure sensor portion 441 and the second pressure sensor portion 461 are coupled to each other (e.g., bonded to each other) to provide the gap 476 between the diaphragm electrode 472 and the signal electrode 474, and as such form gap capacitor 432.

The gap capacitor 432 differs from that described with reference to FIG. 4C in that the techniques for creating gap 476 are different. For example, the gap 476 is created not only by one or more layers 442 being formed on the glass substrate 481 (e.g., patterned layers creating a portion of gap 476), but also by definition of recess 459 in silicon substrate 410 along axis 497. Still further, for example, one or more other material layers (e.g., oxide layer, adhesion layer, etc.) such as patterned layer 485 may be used, for example, to promote adhesion in a particular bonding process, to increase the gap distance between the signal electrode 474 and diaphragm electrode 472, etc.

Still further, as shown in FIG. 5B, the diaphragm 472 (e.g., the thickness thereof) may be defined by the definition of recess 459 in the surface of the silicon substrate 410 facing gap 476. However, the thickness of the diaphragm may be formed by a silicon substrate thickness that has no recesses defined therein and, with or without any other layers formed thereon (e.g., such as shown in FIG. 4C where an unetched silicon substrate 110 forms the diaphragm 72 with an oxide layer 116 formed thereon). Still further, although not shown in FIG. 5B, the diaphragm 472 (e.g., the thickness thereof lying along axis 497) may be defined by the definition of a recess 479 (shown by the dash line) in the surface of the silicon substrate 410 opposite the silicon surface facing gap 476 alone, or in combination with recess 459 defined in the surface of the silicon substrate 410 facing gap 476.

Still further, unlike shown in FIG. 4C, the diaphragm electrode 472 as shown in FIG. 5B does not include an oxide layer formed on the exterior thereof (surface of the diaphragm electrode opposite the surface adjacent gap 476) which may be in contact with the body when used (e.g., putting the surrounding body tissue at ground potential).

As will be discerned from the description of the various embodiments herein, the gap of the gap capacitor may be provided in one or more different manners. For example, the first pressure sensor portion may include a substrate material having a recess funned therein to provide at least a part of the gap between the diaphragm electrode and the signal electrode, such as shown, for example, in FIGS. 5A-5B and FIGS. 6A-6B (e.g., a silicon substrate material may have a recess formed therein to provide at least a part of the gap). Further, the second pressure sensor portion may include a substrate material that provides a cavity formed therein to provide at least a part of the gap between the diaphragm electrode and the signal electrode, such as described (but not shown) with reference to FIG. 4C (e.g., a glass substrate material may provide a cavity defined therein to provide at least a part of the gap between the diaphragm electrode and the signal electrode). Still further, at least one of the first and second pressure sensor portions may include one or more patterned layers formed on a substrate material thereof defining at least one opening to provide at least a part of the gap between the diaphragm electrode and the signal electrode such as shown at least in FIGS. 4C, 5A-5B, and 6A-6B.

As described herein with reference to FIGS. 1-6, the various embodiments of the pressure sensor apparatus may be provided as part of, for example, an implantable lead 10. However, the structure and techniques for reducing parasitic capacitance effects described with reference to FIGS. 1-6 are also applicable to embodiments of wireless pressure sensor apparatus such as shall be described with reference to FIGS. 7A-7C. Likewise, the features described with reference to FIGS. 7A-7C are applicable to the other embodiments described herein with reference to FIGS. 1-6.

Figure 7A:
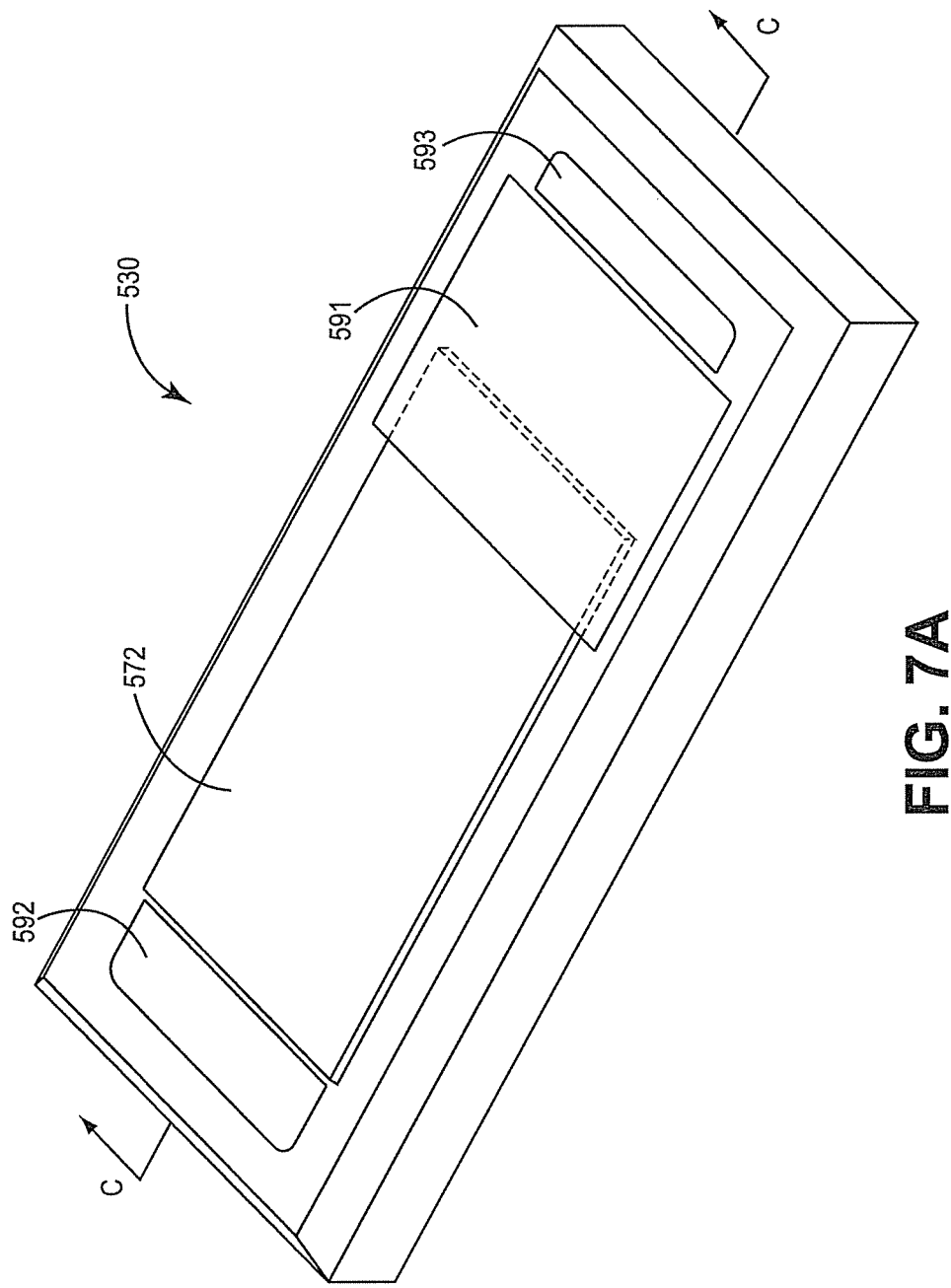
FIG. 7A is a perspective view of one embodiment of a wireless pressure sensor apparatus incorporating concepts and techniques used to reduce parasitic capacitance effects.

FIG. 7A is a perspective view of one embodiment of a wireless pressure sensor apparatus 530 incorporating concepts and techniques used to reduce parasitic capacitance effects. FIG. 7B is another perspective view of the pressure sensor apparatus 530 shown in FIG. 7A with portions of the interior thereof shown in further detail. FIG. 7C is an illustrative section view of the pressure sensor apparatus shown in FIG. 7A and FIG. 7B showing various portions thereof illustratively; some of which, but not necessarily all of which, lie along line C-C of FIG. 7A. FIG. 7C is not a true cross-section view along line C-C of FIG. 7A. For example, as will be apparent, thickness of layers are not provided to scale, additional items may be found in FIG. 7A that are not in the cross-section view, etc.

Generally, the pressure sensor apparatus 530 (e.g., wireless implantable pressure sensor) includes a first pressure sensor portion 541 including a diaphragm electrode 572 connectable to ground. The diaphragm electrode 572 is positioned in close proximity to the body when implanted therein such that the diaphragm electrode 572 is deformable in response to pressure applied thereto by the body, e.g., tissue or fluids. The pressure sensor apparatus 530 further includes a second pressure sensor portion 561 that includes a signal electrode 574. The first pressure sensor portion 541 and the second pressure sensor portion 561 are coupled to each other (e.g., bonded to each other) to provide gap 576 between the diaphragm electrode 572 and the signal electrode 574, and as such forming gap capacitor 532. The second pressure sensor portion 561 further includes an insulator material 578 (e.g., a glass substrate). The signal electrode 574 is provided on and in direct contact with the insulator material 578 to electrically isolate the signal electrode 574 such that parasitic capacitance effects on the signal electrode 574 caused by electrical activity in the body when the pressure sensor apparatus 530 is implanted therein are reduced. Further, the diaphragm electrode 572 is grounded when the implantable pressure sensor apparatus 530 is implanted in the body to shield the signal electrode 572 from electrical activity (e.g., noise) in the body.

Figure 7B:
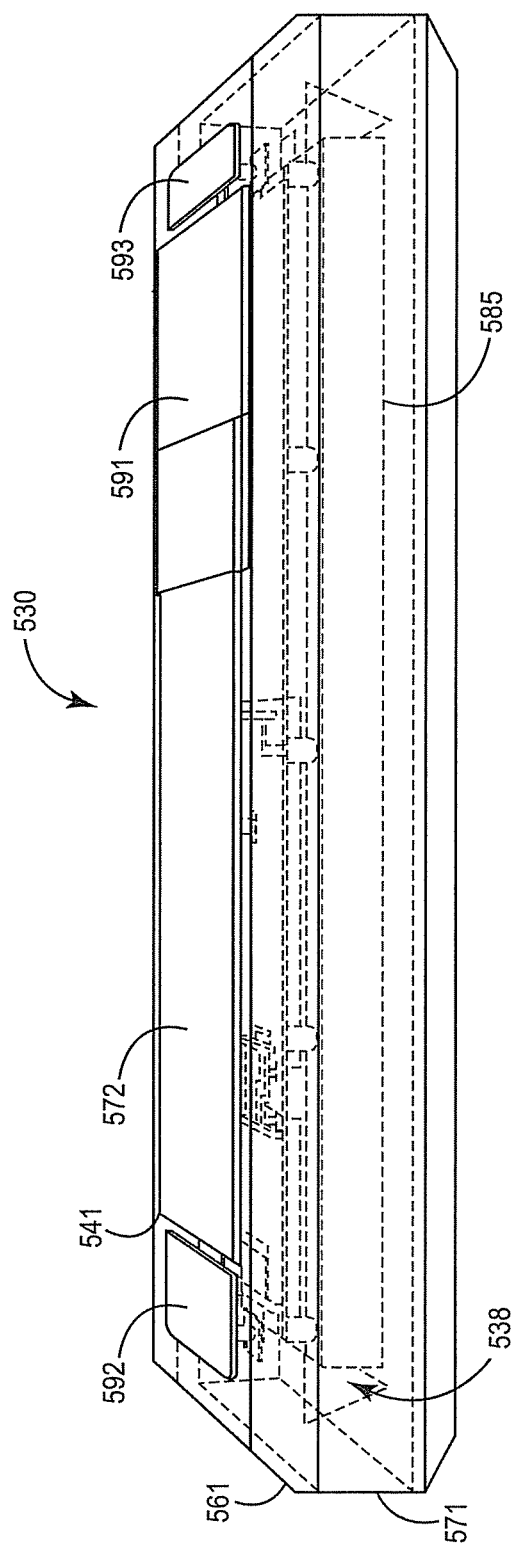
FIG. 7B is another perspective view of the pressure sensor apparatus shown in FIG. 7A with portions of the interior thereof shown in further detail.
Figure 7C:
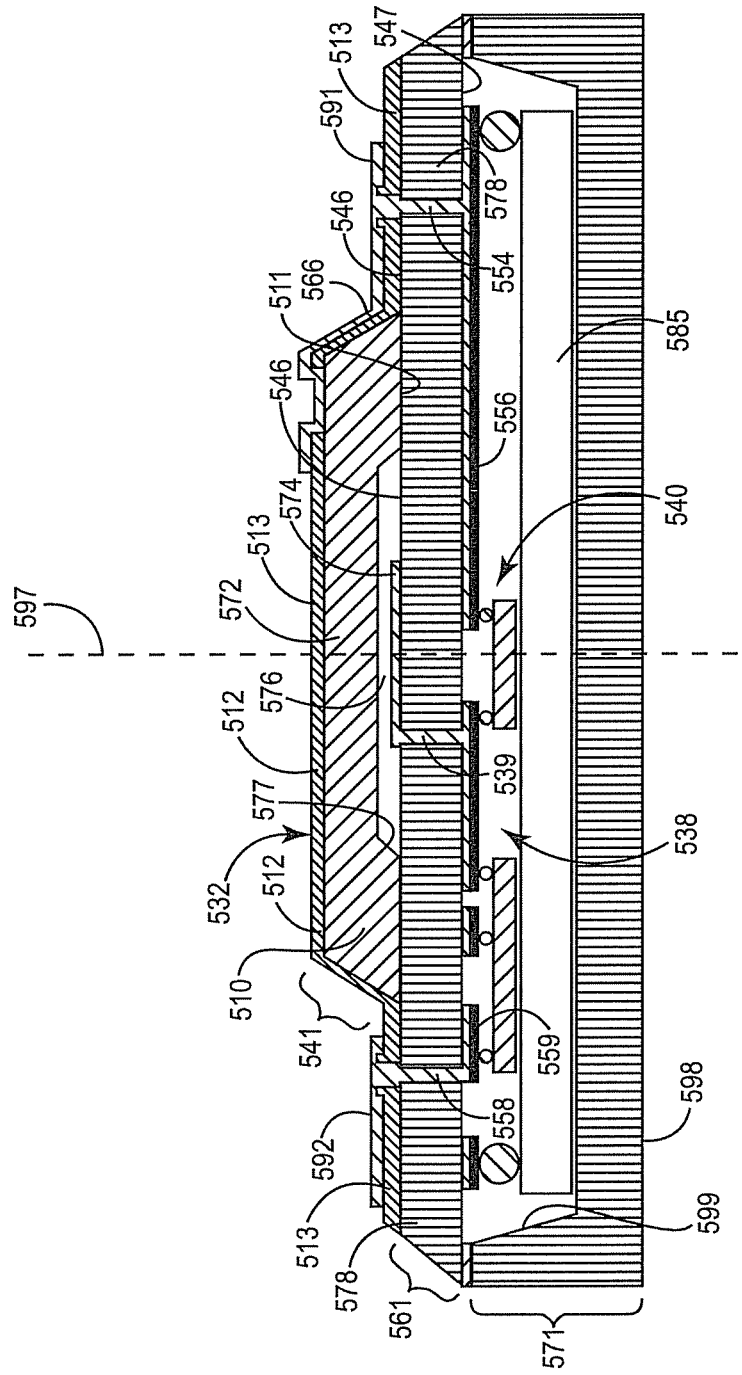
FIG. 7C is a cross-section view of the pressure sensor apparatus shown in FIG. 7A and FIG. 7B showing various portions thereof illustratively; some of which, but not necessarily all of which, lie along line C-C of FIG. 7A.

As shown in FIGS. 7A-7C, in one embodiment, the gap capacitor 532 is formed along an axis 597 when first pressure sensor portion 541 is bonded to second pressure sensor portion 561 (e.g., the diaphragm electrode 572 is centered along axis 597 with signal electrode 574 but separated by gap 576). In this illustrative embodiment, first pressure sensor portion 541 includes silicon substrate 510 (e.g., a planar silicon substrate having a first side surface 511 and a second side surface 512 opposite the first side surface 511) having a recess 577 defined therein (e.g., defined in first side surface 511). The recess 577 formed in the silicon material 510 defines the size of the diaphragm electrode 572. The diaphragm electrode 572 has a cross-sectional area orthogonal to the axis 597 and is generally deformable upon application of external pressure across this cross-sectional area, e.g., external pressure from one or more parts of the body when implanted therein. In FIG. 5C, the shape of the recess 577 is generally rectangular providing a diaphragm electrode 572 that is generally rectangular as shown in FIG. 7B.

The second pressure sensor portion 561 in this illustrative embodiment is formed of a glass substrate 578 on which signal electrode 574 is formed. The glass substrate 578 includes a first side surface 546 to be bonded to the first pressure sensor portion 541 that includes the diaphragm electrode 572 and a second side surface 547 opposite the first side surface 546. For example, as shown in FIG. 7C, conductive material (e.g., gold) may be patterned on the glass substrate 578 to define the size of the signal electrode 574 (e.g., may be patterned using any conductive material patterning processes). The signal electrode 574 has a cross-sectional area orthogonal to the axis 97 and is formed on and in direct contact with the glass substrate 578. In FIG. 7C, although not shown in its entirety, the shape of the signal electrode 574 is generally rectangular and, at least in one embodiment, is generally configured as previously described with reference to FIG. 4C. The diaphragm electrode 572 of the first pressure sensor portion 541 is supported at its periphery over the signal electrode 574 by silicon which is bonded to glass substrate 578 of the second pressure sensor portion 561 (e.g., creating gap 576).

In at least one embodiment, the first pressure sensor portion 541 is sized to be smaller than the second pressure sensor portion 561 such that when bonded to each other they provide area for creation of additional contacts 591-593 (e.g., ground contact, communication electrode, charging electrode, etc.), for example, at the periphery of the first side surface 546 of the glass substrate 578 of the second pressure sensor portion 561. For example, with the first pressure sensor portion 541 coupled to the second pressure sensor portion 561 (e.g., bonded to each other) to provide the gap 576 between the diaphragm electrode 572 and the signal electrode 574, and as such forming gap capacitor 532, one or more layers (e.g., patterned layers) may be formed on the diaphragm electrode 572 and peripheral portions of the first side surface 546 of the glass substrate 578. For example, as shown in FIG. 7C, an oxide layer 513 (e.g., a thermal oxide layer, silicon oxide, etc.) may be formed thereover. One or more patterning processes may be used on the oxide layer 513 for formation of one or more electrical connections (e.g., to provide a ground connection to the diaphragm electrode 572, to provide one or more communication electrodes, etc.)

The coupled first pressure sensor portion 541 and second pressure sensor portion 561 which provides the gap capacitor 532 may also be coupled to a third pressure sensor portion 571 for providing a die cavity 538. For example, the second side surface 547 of the second pressure sensor portion 561 may be bonded to the third pressure sensor portion 571 such that at least one cavity 538 is provided between the second pressure sensor portion 541 and the third pressure sensor portion 571 (e.g., the cavity 538 is formed on the side of second pressure sensor portion opposite the gap capacitor). For example, the third pressure sensor portion 571 may include a glass substrate 598 having a recess 599 formed therein to create die cavity 538 when bonded to second pressure sensor portion 561. Such coupling may be performed as described herein or as described in U.S. Provisional Application No. 61/406,961, filed 26 Oct. 2010, and entitled "Wafer-Scale Package Including Power Source" which is incorporated in its entirety herein, to provide a packaged device similar to that described in U.S. Provisional Application No. 61/406,961. For example, the pressure sensor apparatus 530 may take the form of any of the packaged devices described in U.S. Provisional Application No. 61/406,961 modified by providing a pressure sensor gap capacitor as described herein adjacent to such packages or interface therewith (e.g., creating a gap capacitor on a first substrate and connecting the signal electrode thereof through connection vias formed in that substrate to one or more die mounted in a cavity formed by the first substrate being bonded to another substrate).

One or more die 540 (e.g., one or more integrated circuit die or packages) may be positioned in the cavity 538 between the second pressure sensor portion 561 and third pressure sensor portion 571 with one or more metallization connections provided between the signal electrode 574 and the die cavity 538 for connection of the signal electrode 574 to one or more die positioned in the die cavity 538. Further, as described herein, a power source 585 may be positioned in the at least one die cavity 538, and further the one or more die 540 positioned in the at least one die cavity 538 may be connected such that signals can be transmitted wirelessly from the implantable pressure sensor apparatus 530.

For example, the one or more die 540 (e.g., one or more integrated circuit die or packages) may be used to provide any desired functionality, including that suitable for measuring pressure. For example, the one or more die 540 may include analog/digital integrated circuits that provide signal conditioning functions (e.g., filtering and amplification), signal processing functions, and logic functions. Integrated circuits may also include memory (e.g., volatile/non-volatile) that stores programs used by the integrated circuits to provide the functions associated with the integrated circuits described herein.

The signal electrode 574 provided on and in direct contact with the first side surface 546 of the glass substrate material 578 may be electrically connected to the one or more die 140 of the pressure sensor apparatus 532 using conductive material (e.g., metallization connections 539) provide in openings formed through the glass substrate material 578. For example, die may be mounted on the second side surface 547 of the glass substrate 578 with patterned conductive traces connecting the signal electrode 574 to one or more die in the cavity 538 via the conductive material in the openings 539 (e.g., conductive vias formed through glass substrate 578).

The diaphragm electrode 572 is in contact with ground within the in-vivo environment to shield the signal electrode 574 from noise (e.g., noise due to the electrical activity within the body in which the pressure sensor apparatus 530 is implanted). The diaphragm electrode 572 may be connected to ground contact 591 by conductive trace 566 formed over oxide layer 513. However, the diaphragm electrode 572 may be connected to ground potential by any other manner.

In one or more embodiments, the diaphragm electrode 572 may be in direct contact with the body through a window formed in the oxide layer 113 (e.g., contact with body tissue or fluids). With the diaphragm electrode 572 connected to the ground contact 591, exposure of the diaphragm electrode 572 to the body will put the area of the body in contact with the exposed diaphragm at ground potential. In other words, one or more portions of the diaphragm electrode 572 may not be insulated from the body by the oxide layer 113 shown in FIG. 7C.

As shown in FIG. 7C, ground contact 591 is coupled to one or more die 540 by way of another conductive via 554 formed through the glass substrate 578 and one or more conductive traces 556 formed on the second side surface 547 of the glass substrate 578. Still further, a communication signal contact (or electrode) is also coupled to one or more die 540 by way of another conductive via 558 formed through the glass substrate 578 and one or more conductive traces 559 formed on the second side surface 547 of the glass substrate 578. Further, as shown in FIG. 7C, power source 585 is connected to one or more of the die 540 as well as one or more of the contacts 591, 592, or 593 (e.g., a pad for use in charging the power source).

With the signal electrode being shielded from noise by the grounded diaphragm electrode 572, the signal electrode 574 is also isolated by glass substrate 578 on which it is directly provided (e.g., formed, deposited, patterned, etc.). The glass substrate 578 electrically isolates the signal electrode 572 such that parasitic capacitance effects on the signal electrode 572 caused by electrical activity in the body when the pressure sensor apparatus 530 is implanted therein are reduced. One will recognize that the glass substrate also reduces parasitic capacitance effects with respect to the metallization connection of the signal electrode 572 to the one or more die 540 in the cavity 538.

As illustrated in FIGS. 7A-7C, the pressure sensor apparatus 530 may include the power source 585, and the one or more die 540 may include a control module. The power source 585 may be connected to provide power to components of the pressure sensor apparatus 530 including, for example, a control module, a sensor module, and/or a tissue conduction communication (TCC) module, or any other components, such as described in U.S. Provisional Application No. 61/406,961. Further, the pressure sensor apparatus may communicate information therefrom in any manner as described in U.S. Provisional Application No. 61/406,961, including with use of an antenna, or using tissue conductance communication.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. An implantable capacitive pressure sensor apparatus, comprising:
   a first pressure sensor portion comprising a diaphragm electrode connectable to ground, wherein the diaphragm electrode is positioned in close proximity to the body when implanted therein such that the diaphragm electrode is deformable in response to pressure applied thereto by the body; and
   a second pressure sensor portion comprising:
      a signal electrode, wherein the first pressure sensor portion and the second pressure sensor portion provide a gap between the diaphragm electrode and the signal electrode, and
      an insulator material, wherein the signal electrode is provided on and in direct contact with the insulator material to electrically isolate the signal electrode such that parasitic capacitance effects on the signal electrode caused by electrical activity in the body when the pressure sensor apparatus is implanted therein are reduced, and further wherein the diaphragm electrode is grounded when the implantable pressure sensor apparatus is implanted in the body to shield the signal electrode from electrical activity in the body.

2. The apparatus of claim 1, wherein the second pressure sensor portion comprises a glass substrate material extending from a first side surface to a second side surface opposite the first side surface, and further wherein the signal electrode is provided on and in direct contact with the first side surface of the glass substrate material.

3. The apparatus of claim 2, wherein the signal electrode is provided on and in direct contact with the glass substrate material and electrically connected to one or more die of the pressure sensor apparatus via conductive material patterned on at least a portion of the glass substrate material.

4. The apparatus of claim 2, wherein one or more openings are defined through the glass substrate material, and further wherein the signal electrode is provided on and in direct contact with the glass substrate material and electrically connected to one or more die of the pressure sensor apparatus via conductive material formed in the one or more openings.

5. The apparatus of claim 1, wherein the diaphragm electrode of the first pressure sensor portion lies parallel to the signal electrode of the second pressure sensor portion along an axis of a gap capacitor formed thereby, wherein the diaphragm electrode is deformable over a cross-sectional area orthogonal to the axis, and further wherein the signal electrode provided on and in direct contact with the insulator material has a cross-sectional area orthogonal to the axis that is about the same as, or no more than 95 percent smaller than, the deformable cross-sectional area of the diaphragm electrode orthogonal to the axis.

6. The apparatus of claim 1, wherein the signal electrode is provided on and in direct contact with the insulator material of the second pressure sensor portion to electrically isolate the signal electrode such that parasitic capacitance effects on the signal electrode caused by electrical activity in the body when the pressure sensor apparatus is implanted therein are less than 0.5 times a capacitance of a gap capacitor formed by the diaphragm electrode separated from the signal electrode by the gap.

7. The apparatus of claim 1, wherein the insulator material comprises a glass insulator material, wherein the diaphragm electrode is separated from the signal electrode by a gap distance, and further wherein the glass insulator material has a thickness adjacent the signal electrode that is greater than about 6 times the gap distance separating the diaphragm electrode from the signal electrode.

8. The apparatus of claim 1, wherein the second pressure sensor portion comprises a substrate material comprising at least one trench formed through at least a portion thereof, wherein the at least one trench is filled with the insulator material, and further wherein the signal electrode is provided on and in direct contact with the insulator material.

9. The apparatus of claim 8, wherein the second pressure sensor portion comprises a silicon substrate comprising at least one trench formed therein, wherein the at least one trench is filled with a glass insulator material, and further wherein the signal electrode is provided on and in direct contact with the glass insulator material.

10. The apparatus of claim 8, wherein the at least one trench is formed through an entire thickness thereof, wherein the at least one trench is filled with the insulator material, and further wherein the signal electrode is provided on and in direct contact with the insulator material.

11. The apparatus of claim 10, wherein the second pressure sensor portion comprises a silicon substrate comprising at least one trench formed therein, wherein the at least one trench is filled with a glass insulator material, and further wherein the signal electrode is provided on and in direct contact with the glass insulator material.

12. The apparatus of claim 1, wherein the first pressure sensor portion is bonded to the second pressure sensor portion such that a gap is provided between the diaphragm electrode and the signal electrode.

13. The apparatus of claim 12, wherein the first pressure sensor portion is bonded to the second pressure sensor portion such that at least one die cavity is provided between the first pressure sensor portion and the second pressure sensor portion, wherein one or more metallization connections are provided between the signal electrode and the die cavity for connection of the signal electrode to one or more die positioned in the die cavity, and further wherein the insulator material electrically isolates the one or more metallization connections such that parasitic capacitance effects on the one or more metallization connections caused by electrical activity in the body when the pressure sensor apparatus is implanted therein are reduced.

14. The apparatus of claim 1, wherein the implantable pressure sensor apparatus is provided as part of an implantable medical electrical lead.

15. The apparatus of claim 1, wherein the implantable pressure sensor apparatus is a wireless implantable pressure sensor apparatus.

16. The apparatus of claim 1, wherein the apparatus further comprises a third pressure sensor portion, wherein the second pressure sensor portion is bonded to the third pressure sensor portion such that at least one die cavity is provided between the second pressure sensor portion and the third pressure sensor portion, wherein one or more metallization connections are provided between the signal electrode and the die cavity for connection of the signal electrode to one or more die positioned in the die cavity.

17. The apparatus of claim 16, wherein a power source is positioned in the at least one die cavity, and further wherein the one or more die positioned in the at least one die cavity are connected such that signals can be transmitted wirelessly from the implantable pressure sensor apparatus.

18. The apparatus of claim 1, wherein the first pressure sensor portion comprises a substrate material, wherein the substrate material provides a recess formed therein to provide at least a part of the gap between the diaphragm electrode and the signal electrode.

19. The apparatus of claim 18, wherein the first pressure sensor portion comprises a silicon substrate material, wherein the silicon substrate material provides a recess formed therein to provide at least a part of the gap between the diaphragm electrode and the signal electrode, and further wherein the second pressure sensor portion comprises a planar glass substrate on which the signal electrode is directly provided.

20. The apparatus of claim 1, wherein second pressure sensor portion comprises a substrate material, wherein the substrate material provides a cavity formed therein to provide at least a part of the gap between the diaphragm electrode and the signal electrode.

21. The apparatus of claim 20, wherein second pressure sensor portion comprises a glass substrate material, wherein the glass substrate material provides a cavity defined therein to provide at least a part of the gap between the diaphragm electrode and the signal electrode.

22. The apparatus of claim 1, wherein at least one of the first and second pressure sensor portions comprise one or more patterned layers formed on a substrate material defining at least one opening to provide at least a part of the gap between the diaphragm electrode and the signal electrode.

23. A method of making an implantable capacitive pressure sensor apparatus, the method comprising:
providing a first pressure sensor portion comprising a diaphragm electrode connectable to ground, wherein the diaphragm electrode is positioned in close proximity to the body when implanted therein such that the diaphragm is deformable in response to pressure applied thereto by the body; and
providing a second pressure sensor portion comprising a signal electrode relative to the first pressure sensor portion to provide a gap between the diaphragm electrode and the signal electrode, wherein the second pressure sensor portion further comprises an insulator material, wherein the signal electrode is provided on and in direct contact with the insulator material to electrically isolate the signal electrode such that parasitic capacitance effects on the signal electrode caused by electrical activity in the body when the pressure sensor apparatus is implanted therein are reduced, and further wherein the diaphragm electrode is grounded when the implantable pressure sensor apparatus is implanted in the body to shield the signal electrode from electrical activity in the body.

24. The method of claim 23, wherein providing the second pressure sensor portion comprises providing a glass substrate material extending from a first side surface to a second side surface opposite the first side surface, and further wherein the signal electrode is formed on and in direct contact with first side surface of the glass substrate material.

25. The method of claim 24, wherein the method further comprises electrically connecting the signal electrode provided on and in direct contact with the glass substrate material to one or more die of the pressure sensor apparatus via conductive material patterned on at least a portion of the glass substrate material.

26. The method of claim 24, wherein the method further comprises defining one or more openings through the glass substrate material, and electrically connecting the signal electrode provided on and in direct contact with the glass substrate material to one or more die of the pressure sensor apparatus via conductive material formed in the one or more openings.

27. The method of claim 23, wherein providing the second pressure sensor portion comprises:
providing a substrate material;
defining at least one trench through at least a portion thereof; and
filling the at least one trench with the insulator material, wherein the signal electrode is formed on and in direct contact with the insulator material.

28. The method of claim 27, wherein the substrate material comprises a silicon substrate material, and further wherein the insulator material comprises a glass insulator material, wherein the signal electrode is formed on and in direct contact with the glass insulator material.

29. The method of claim 27, wherein defining the at least one trench comprises defining that at least one trench through an entire thickness thereof, wherein the at least one trench is filled with the insulator material, and further wherein the signal electrode is provided on and in direct contact with the insulator material.

30. The method of claim 27, wherein defining the at least one trench comprises defining at least one trench through the back side of a silicon substrate material, wherein the at least one trench is filled with a glass insulator material, and further wherein the signal electrode is provided on and in direct contact with the glass insulator material.

31. The method of claim 23, wherein the method further comprises bonding the first pressure sensor portion to the second pressure sensor portion such that a gap is provided between the diaphragm electrode and the signal electrode.

32. The method of claim 31, wherein bonding the first pressure sensor portion to the second pressure sensor portion further defines at least one die cavity provided between the first pressure sensor portion and the second pressure sensor portion, and wherein the method further comprises:
forming one or more metallization connections between the signal electrode and die cavity for connection of the signal electrode to one or more die positioned in the die cavity; and
electrically isolating the one or more metallization connections using the insulator material.

33. The method of claim 23, wherein the method further comprises:
    providing a third pressure sensor portion;
    bonding the second pressure sensor portion to the third pressure sensor portion such that at least one die cavity is provided between the second pressure sensor portion and the third pressure sensor portion; and
    forming one or more metallization connections between the signal electrode and die cavity for connection of the signal electrode to one or more die positioned in the die cavity.

34. The method of claim 33, wherein the method further comprises providing a power source in the at least one die cavity, and connecting the one or more die positioned in the at least one die cavity such that signals can be transmitted wirelessly from the pressure sensor apparatus.

35. The method of claim 23, wherein providing the first pressure sensor portion comprises:
    providing a substrate material;
    defining a recess in the substrate material to provide at least a part of the gap between the diaphragm electrode and the signal electrode.

36. The method of claim 35, wherein providing the substrate material comprises providing a silicon substrate material, wherein the recess is defined in the silicon substrate material to provide at least a part of the gap between the diaphragm electrode and the signal electrode, and further wherein providing the second pressure sensor portion comprises providing a planar glass substrate material upon which the signal electrode is directly provided.

37. The method of claim 23, wherein providing the second pressure sensor portion comprises:
    providing a substrate material; and
    defining a recess in the substrate material to provide at least a part of the gap between the diaphragm electrode and the signal electrode.

38. The method of claim 37, wherein providing the substrate material comprises providing a glass substrate material, wherein the recess is defined in the glass substrate material to provide at least a part of the gap between the diaphragm electrode and the signal electrode.

39. The method of claim 23, wherein providing at least one of the first pressure sensor portion and the second pressure sensor portion comprises:
    providing a substrate material; and
    patterning one or more layers formed on the substrate material to define at least one opening to provide at least a part of the gap between the diaphragm electrode and the signal electrode.

* * * * *